US012767976B2

(12) United States Patent
Allawi et al.

(10) Patent No.: US 12,767,976 B2
(45) Date of Patent: *Oct. 20, 2026

(54) NUCLEIC ACID CONTROL MOLECULES FROM NON-HUMAN ORGANISMS

(71) Applicant: Exact Sciences Corporation, Madison, WI (US)

(72) Inventors: Hatim T. Allawi, Middleton, WI (US); Graham P. Lidgard, Middleton, WI (US); Brian Aizenstein, Madison, WI (US); Melissa M. Gray, Madison, WI (US)

(73) Assignee: Exact Sciences Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/589,016

(22) Filed: Feb. 27, 2024

(65) Prior Publication Data

US 2024/0309426 A1 Sep. 19, 2024

Related U.S. Application Data

(60) Continuation of application No. 17/529,896, filed on Nov. 18, 2021, now Pat. No. 11,952,615, which is a division of application No. 16/318,578, filed as application No. PCT/US2017/042842 on Jul. 19, 2017, now Pat. No. 11,208,680.

(60) Provisional application No. 62/364,049, filed on Jul. 19, 2016.

(51) Int. Cl.
*C12Q 1/6806* (2018.01)
*C12N 15/10* (2006.01)

(52) U.S. Cl.
CPC ....... *C12Q 1/6806* (2013.01); *C12N 15/1006* (2013.01); *C12Q 2600/154* (2013.01); *C12Q 2600/16* (2013.01)

(58) Field of Classification Search
CPC ...................... C12Q 2600/16; C12Q 2600/154
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,965,188 | A | 10/1990 | Mullis et al. |
| 5,011,769 | A | 4/1991 | Duck et al. |
| 5,124,246 | A | 6/1992 | Urdea et al. |
| 5,288,609 | A | 2/1994 | Engelhardt et al. |
| 5,338,671 | A | 8/1994 | Scalice et al. |
| 5,403,711 | A | 4/1995 | Walder et al. |
| 5,409,818 | A | 4/1995 | Davey et al. |
| 5,494,810 | A | 2/1996 | Barany et al. |
| 5,508,169 | A | 4/1996 | Deugau et al. |
| 5,624,802 | A | 4/1997 | Urdea et al. |
| 5,639,611 | A | 6/1997 | Wallace et al. |
| 5,660,988 | A | 8/1997 | Duck et al. |
| 5,670,325 | A | 9/1997 | Lapidus et al. |
| 5,710,264 | A | 1/1998 | Urdea et al. |
| 5,741,650 | A | 4/1998 | Lapidus et al. |
| 5,773,258 | A | 6/1998 | Birch et al. |
| 5,792,614 | A | 8/1998 | Western et al. |
| 5,830,665 | A | 11/1998 | Shuber et al. |
| 5,846,717 | A | 12/1998 | Brow et al. |
| 5,849,481 | A | 12/1998 | Urdea et al. |
| 5,851,770 | A | 12/1998 | Babon et al. |
| 5,882,867 | A | 3/1999 | Ullman et al. |
| 5,888,778 | A | 3/1999 | Shuber |
| 5,914,230 | A | 6/1999 | Liu et al. |
| 5,928,870 | A | 7/1999 | Lapidus et al. |
| 5,952,178 | A | 9/1999 | Lapidus et al. |
| 5,958,692 | A | 9/1999 | Cotton et al. |
| 5,965,408 | A | 10/1999 | Short |
| 5,985,557 | A | 11/1999 | Prudent et al. |
| 5,994,069 | A | 11/1999 | Hall et al. |
| 6,001,567 | A | 12/1999 | Brow et al. |
| 6,013,170 | A | 1/2000 | Meade |
| 6,020,137 | A | 2/2000 | Lapidus et al. |
| 6,063,573 | A | 5/2000 | Kayyem |
| 6,090,543 | A | 7/2000 | Prudent et al. |
| 6,110,677 | A | 8/2000 | Western et al. |
| 6,110,684 | A | 8/2000 | Kemper et al. |
| 6,121,001 | A | 9/2000 | Western et al. |
| 6,143,529 | A | 11/2000 | Lapidus et al. |

(Continued)

FOREIGN PATENT DOCUMENTS

| | | |
|---|---|---|
| CN | 101675171 A | 3/2010 |
| WO | WO 2002/070755 | 9/2002 |
| WO | WO 2005/023091 | 3/2005 |
| WO | WO 2005/038051 | 4/2005 |
| WO | WO 2005/098050 | 10/2005 |
| WO | WO 2006/113770 | 10/2006 |
| WO | WO 2013/116375 | 8/2013 |
| WO | WO 2017/075061 | 5/2017 |

(Continued)

OTHER PUBLICATIONS

Ballabio, et al., Screening for steroid sulfatase (STS) gene deletions by multiplex DNA amplification, Human Genetics, 1990, 84(6): 571-573.

(Continued)

*Primary Examiner* — Joseph G. Dauner
(74) *Attorney, Agent, or Firm* — Casimir Jones, S.C.; Mary Ann D. Brow

(57) ABSTRACT

The present invention provides synthetic DNA strands that find use as process controls in DNA processing and nucleic acid testing methods. In particular, provided herein are synthetic methylated DNA strands of known composition for use as control molecules in DNA testing, e.g., of mutations and/or methylation of DNA isolated from non-fish samples, such as human samples.

19 Claims, 9 Drawing Sheets

Specification includes a Sequence Listing.

(56) References Cited

U.S. PATENT DOCUMENTS 6,146,828 A 11/2000 Lapidus et al.
6,150,097 A 11/2000 Tyagi et al.
6,183,960 B1 2/2001 Lizardi
6,203,993 B1 3/2001 Shuber et al.
6,210,884 B1 4/2001 Lizardi
6,221,583 B1 4/2001 Kayyem et al.
6,235,502 B1 5/2001 Weissman et al.
6,248,229 B1 6/2001 Meade
6,268,136 B1 7/2001 Shuber et al.
6,280,947 B1 8/2001 Shuber et al.
6,300,077 B1 10/2001 Shuber et al.
6,303,304 B1 10/2001 Shuber et al.
6,351,857 B2 3/2002 Slaon, III et al.
6,406,857 B1 6/2002 Shuber et al.
6,415,455 B1 7/2002 Slaon, III et al.
6,428,964 B1 8/2002 Shuber
6,475,738 B2 11/2002 Shuber et al.
6,482,595 B2 11/2002 Shuber et al.
6,498,012 B2 12/2002 Laken
6,503,718 B2 1/2003 Shuber et al.
6,551,777 B1 4/2003 Shuber et al.
6,586,177 B1 7/2003 Shuber
6,750,020 B2 6/2004 Shuber
6,818,404 B2 11/2004 Shuber
6,844,155 B2 1/2005 Shuber
6,849,403 B1 2/2005 Shuber
6,872,816 B1 3/2005 Hall et al.
6,919,174 B1 7/2005 Shuber
6,964,846 B1 11/2005 Shuber
7,368,233 B2 5/2008 Shuber et al.
7,662,594 B2 2/2010 Kong et al.
7,981,612 B2 7/2011 Shuber et al.
8,361,720 B2 1/2013 Oldham-Haltom et al.
8,715,937 B2 5/2014 Zou et al.
8,916,344 B2 12/2014 Zou et al.
9,096,893 B2 8/2015 Allawi et al.
9,212,392 B2 12/2015 Allawi et al.
9,315,853 B2 4/2016 Domanico et al.
10,385,406 B2 * 8/2019 Allawi ................. C12Q 1/6806
10,704,081 B2 * 7/2020 Lidgard ............... C12Q 1/6806
10,822,638 B2 * 11/2020 Allawi ................... C12Q 1/686
11,028,447 B2 * 6/2021 Allawi ................. C12Q 1/6806
11,299,766 B2 * 4/2022 Lidgard ............. C12N 15/1006
11,674,168 B2 * 6/2023 Allawi ............... C12N 15/1006 506/9
2004/0241658 A1 12/2004 Barrett et al.
2007/0202525 A1 8/2007 Quake et al.
2009/0253142 A1 10/2009 Allawi et al.
2012/0322072 A1 12/2012 Nygren
2017/0121704 A1 * 5/2017 Allawi ................. C12Q 1/6806
2017/0121757 A1 * 5/2017 Lidgard ............. C12N 15/1006
2017/0335401 A1 * 11/2017 Allawi ................. C12Q 1/6806
2019/0330702 A1 * 10/2019 Allawi ................. C12Q 1/6806
2020/0040377 A1 2/2020 Allawi et al.
2020/0291458 A1 * 9/2020 Lidgard ................. C12Q 1/686
2021/0079451 A1 * 3/2021 Allawi ................. C12Q 1/6806
2021/0262042 A1 * 8/2021 Allawi ................. C12Q 1/6886
2022/0267831 A1 * 8/2022 Lidgard ............... C12Q 1/6806
2023/0392189 A1 * 12/2023 Allawi ................. C12Q 1/6806
2025/0084455 A1 * 3/2025 Lidgard ............... C12Q 1/6806

FOREIGN PATENT DOCUMENTS

WO WO-2017075061 A1 * 5/2017 ........... C12Q 1/6837
WO WO-2017192221 A1 * 11/2017 ........... C12Q 1/6806
WO WO 2018/140781 8/2018

OTHER PUBLICATIONS

Barany, Genetic disease detection and DNA amplification using cloned thermostable ligase, Proc. Natl. Acad. Sci USA, 1991, 88:189-93.

Bustin, Absolute quantification of mRNA using real-time reverse transcription polymerase chain reaction assays, J. Molecular Endocrinology, 2000, 25:169-193.

Ceska et al., Structure-specific DNA cleavage by 5' nucleases. Trends Biochem Sci. Sep. 1998;23(9):331-6.

Chamberlain et al., Deletion screening of the Duchenne muscular dystrophy locus via multiplex DNA amplification, Nucleic Acids Research, 1988, 16(23):11141-11156.

Diffenbach and Dveksler, PCR Primer, A Laboratory Manual, Cold Spring Harbor Press 1995, TOC Only.

Don et al., 'Touchdown' PCR to circumvent spurious priming during gene amplification, Nucleic Acids Research, 1991, 19(14):4008.

Fang et al., Global and gene specific DNA methylation changes during zebrafish development. Comp Biochem Physiol B Biochem Mol Biol. Sep. 2013;166(1):99-108.

GENBANK Accession No. BC081661.1, Danio rerio Ras association (RaIGDS/AF-6) domain family 1, mRNA, 2007, 2 pages.

GENBANK Accession No. BX465868.6, Zebrafish DNA sequence from clone DKEY-4219 in linkage gropu 22, 2015, 48 pages.

GENBANK Accession No. EH439764.1, FDR103-P00023-DEPE-F_G22 FDR103 Danio rerio cDNA clone FDR103-P00023-BR_G22 5-mRNA sequence, 2007, 2 pages.

Goll et al., DNA Methylation in Zebrafish. Prog Mol Biol Transl Sci. 2011;101:193-218.

Guilfoyle et al., Ligation-mediated PCR amplification of specific fragments from a class-II restriction endonuclease total digest, Nucleic Acids Research, 1997, 25:1854-1858.

Hall et al., Sensitive detection of DNA polymorphisms by the serial invasive signal amplification reaction, PNAS, 2000, 97:8272.

Hao et al., Generation and Characterization of a genetic zebrafish model of SMA carrying the human SMN2 gene. Mol Neurodegener. Mar. 28, 2011;6(1):24.

Hayden et al., Multiplex-Ready PCR: A new method for multiplexed SSR and SNP genotyping, BMC Genomics, 2008, 9:80.

Hecker et al., High and low annealing temperatures increase both specificity and yield in touchdown and stepdown PCR, Biotechniques, 1996, 20(3):478-485.

Herman et al., Methylation-specific PCR: a novel PCR assay for methylation status of CpG islands. Proc Natl Acad Sci USA 1996; 93: 9821-9826.

Higuchi et al., A general method of in vitro preparation and specific mutagenesis of DNA fragments: study of protein and DNA interactions, Nucleic Acids Research, 1988, 16(15):7351-7367.

Higuchi et al., Simultaneous amplification and detection of specific DNA sequences, Biotechnology, 1992, 10:413-417.

Higuchi et al.,Kinetic PCR analysis: real-time monitoring of DNA amplification reactions, Biotechnology, 1993, 11:1026-1030.

Kaiser et al., A comparison of eubacterial and archaeal structure-specific 5'-exonucleases. J Biol Chem. Jul. 23, 1999;274(30):21387-94.

Kalinina et al., Nanoliter scale PCR with TaqMan detection, Nucleic Acids Research, 1997, 25:1999-2004.

Korbie et al., Multiplex bisulfite PCR resequencing of clinical FFPE DNA. Clin Epigenetics. Mar. 17, 2015;7(1):28.

Kwok et al., Effects of primer-template mismatches on the polymerase chain reaction: human immunodeficiency virus type 1 model studies. Nucleic Acids Res. Feb. 25, 1990;18(4):999-1005.

Lage et al., Whole genome analysis of genetic alterations in small DNA samples using hyperbranched strand displacement amplification and array-CGH. Genome Res. Feb. 2003;13(2):294-307.

Liu et al., Flap endonuclease 1: a central component of DNA metabolism. Annu Rev Biochem. 2004;73:589-615.

Lyamichev et al.,Polymorphism identification and quantitative detection of genomic DNA by invasive cleavage of oligonucleotide probes, Nat. Biotech., 1999, 17:292-296.

Mhanni, Characterization of DNA Methylation in the Zebrafish, Danio rerio: Implications for Zebarfish Use as a Model System to Study the Role of DNA Methylation in Normal and Abnormal Development. Ph.D. Thesis, University of Manitoba. Dec. 2002. 8 pages.

(56) References Cited

OTHER PUBLICATIONS

Olivier, The Invader assay for SNP genotyping, Mutat Res. Jun. 3, 2005;573(1-2):103-10.
Olkhov-Mitsel et al., Novel multiplex MethyLight protocol for detection of DNA methylation in patient tissues and bodily fluids. Sci Rep. Mar. 21, 2014;4:4432.
Orpana, Fluorescence resonance energy transfer (FRET) using ssDNA binding fluorescent dye, Biomol Eng. Apr. 2004;21(2):45-50.
R. Rapley, The Nucleic Acid Protocols Handbook 2000, Humana Press, Totowa, N.J, Toc Only.
Roux, Using mismatched primer-template pairs in touchdown PCR, Biotechniques, 1994, 16(5):812-814.
Schouten et al., Relative quantification of 40 nucleic acid sequences by multiplex ligation-dependent probe amplification, Nucleic Acids Research, 2002, 30(12): e57.
Selvin, Fluorescence resonance energy transfer, 1995, Methods Enzymol. 1995;246:300-34.
Stryer, Fluorescence energy transfer as a spectroscopic ruler, Annu Rev Biochem. 1978;47:819-46.
Tollefsbol et al., Control of methylation spreading in synthetic DNA sequences by the murine DNA methyltransferase. J Mol Biol. Jun. 20, 1997;269(4):494-504.
Triglia et al., A procedure for in vitro amplification of DNA segments that lie outside the boundaries of known sequences, Nucleic Acids Res., 1988, 16:8186.
Vogelstein et al. Digital PCR. Proc Natl Acad Sci USA. 1999;96; 9236-41.
Extended EP Search Report for EP17831787.1, mailed Dec. 20, 2019, 15 pages.
International Search Report and Written Opinion for PCT/US2017/042842, mailed Nov. 29, 2017, 20 pages.

* cited by examiner

FIG. 1

*Danio rerio (Zebrafish) RASSF1*

Untreated Target (UT) Target Sequence (SEQ ID NO: 2)

ATCAGAACGAGACGCTAAATTTATCAGCTTGCTTTGGAGTAAACAGCGTTGCTTTAAAACACTCCACAGTCATAAATCATCTCCAGCCC
TAACCATGGTCCACTGAGCCATGCCGTTCATCCTCCCACGATCCCAAAATGGCAAAATGTGAGCTCATCGAGTTGCAGGACTTGACTCC
GAATGACCGTATTGAGCTGGCACCCCCTAGTGTCCCTCCACCCACCGTGGTGCCCACTCTGGACAGGTGGAGCAGAGGGAAGGTGGTGC
GCATGGTGGGCGAGCGCGTGCGCCTGGAGGACCCCGATTGGCTGACGTGTAAACCAGGACGAGGACATGACTTTCAGCCCTGCAGCCAG
ACACAGCTGAGCTGGTGTGACCTGTGTGGAGAGTTCATCTGGGGCCTGTACAGACAGAGCCTCC

Bisulfite-treated (BT) Target Sequence(SEQ ID NO: 3)

ATTAGAACGAGACGTTAAATTTATTAGTTTGTTTTGGAGTAAATAGCGTTGTTTTAAAATATTTTATAGTTATAAATTATTTTTAGTTT
TAATTATGGTTTATTGAGTTATGTCGTTTATTTTTTTACGATTTTAAAATGGTAAAATGTGAGTTTATCGAGTTGTAGGATTTGATTTC
GAATGATCGTATTGAGTTGGTATTTTTTAGTGTTTTTTTATTTATCGTGGTGTTTATTTTGGATAGGTGGAGTAGAGGGAAGGTGGTGC
GTATGGTGGGCGAGCGCGTGCGTTTGGAGGATTTCGATTGGTTGACGTGTAAATTAGGACGAGGATATGATTTTTAGTTTTGTAGTTAG
ATATAGTTGAGTTGGTGTGATTTGTGTGGAGAGTTTATTTGGGGTTTGTATAGATAGAGTTTTC

QuARTS flap endonuclease assay oligonucleotides:

For untreated target DNA

| | | |
|---|---|---|
| ZF_RASSF1 UT forward primer | 5'CGCATGGTGGGCGAG3' | (SEQ ID NO: 4) |
| ZF_RASSF1 UT reverse primer | 5'ACACGTCAGCCAATCGGG3' | (SEQ ID NO: 5) |
| ZF_RASSF1 UT Probe (Arm 7 underlined) | 5'GCGCGTCCGCGCGTGCGCC/3C6/ | (SEQ ID NO: 23) |

For bisulfite-converted target DNA

| | | |
|---|---|---|
| ZF_RASSF1 BT forward primer | 5'TGCGTATGGTGGGCGAG3' | (SEQ ID NO: 7) |
| ZF_RASSF1 BT reverse primer | 5'CCTAATTTACACGTCAACCAATCGAA3' | (SEQ ID NO: 8) |
| ZF_RASSF1 BT probe (Arm 3 underlined) | 5'GACGCGGAGGCGCGTGCGTTT/3C6/ | (SEQ ID NO: 9) |
| ZF_RASSF1 BT probe (Arm 5 underlined) | 5'CCACGGACGGCGCGTGCGTTT/3C6/ | (SEQ ID NO: 10) |

FIG. 2

*Single-stranded Synthetic Methylated Zebrafish RASSF1 Oligonucleotides*

Sense 180; 171 nucleotides (SEQ ID NO: 11)

5′ TCCAC/iMe-dC/GTGGTGCCCACTCTGGACAGGTGGAGCAGAGGGAAGGTGGTG/iMe-dC/GCATGGTGGG/iMe-dC/GAG
/iMe-dC/G/iMe-dC/GTG/iMe-dC/GCCTGGAGGACCC/iMe-dC/GATTGGCTGA/iMe-dC/GTGTAAACCAGGA/iMe-dC/
GAGGACATGACTTTCAGCCCTGCAGCCAGACACAGCTGAGCTGGTGTGACCTGTGTGGAGAGTTCATCTGG 3′

Antisense 180; 171 nucleotides (SEQ ID NO: 12)

5′ CCAGATGAACTCTCCACACAGGTCACACCAGCTCAGCTGTGTCTGGCTGCAGGGCTGAAAGTCATGTCCT/iMe-dC/GTCCTGG
TTTACA/iMe-dC/GTCAGCCAAT/iMe-dC/GGGGTCCTCCAGG/iMe-dC/GCA/iMe-dC/G/iMe-dC/GCT/iMe-dC/GCCC
ACCATG/iMe-dC/GCACCACCTTCCCTCTGCTCCACCTGTCCAGAGTGGGCACCA/iMe-dC/GGTGGA 3′

FIG. 5

*β-actin Target DNAs*

Untreated Target (UT) Sequence (SEQ ID NO: 13)

5′CTCTGACCTGAGTCTCCTTTGGAACTCTGCAGGTTCTATTTGCTTTTTCCCAGATGAGCTCTTTTTCTGGTGTTTGTCTCTCTGACT
AGGTGTCTAAGACAGTGTTGTGGGTGTAGGTACTAACACTGGCTCGTGTGACAAGGCCATGAGGCTGGTGTAAAGCGGCCTTGGAGTGT
GTATTAAGTAGGTGCACAGTAGGTCTGAACAGACTCCCCATCCCAAGA3′

Bisulfite-treated (BT) Target Sequence (SEQ ID NO: 14)

5′TTTTGATTTGAGTTTTTTTTGGAATTTTGTAGGTTTTATTTGTTTTTTTTTAGATGAGTTTTTTTTTGGTGTTTGTTTTTTTGATT
AGGTGTTTAAGATAGTGTTGTGGGTGTAGGTATTAATATTGGTTTGTGTGATAAGGTTATGAGGTTGGTGTAAAGTGGTTTTGGAGTGT
GTATTAAGTAGGTGTATAGTAGGTTTGAATAGATTTTTTATTTTAAGA3′

QuARTS flap endonuclease assay oligonucleotides:

For untreated target DNA

| | |
|---|---|
| β-actin UT forward primer | 5′ CCATGAGGCTGGTGTAAAG3′ (SEQ ID NO: 15) |
| β-actin UT reverse primer | 5′ CTACTGTGCACCTACTTAATACAC3′ (SEQ ID NO: 16) |
| β-actin UT Probe (Arm 1 underlined) | 5′ CGCCGAGGGCGGCCTTGGAG/3C6/ (SEQ ID NO: 17) |

FIG. 5 cont'd

For bisulfite-converted target DNA

| | |
|---|---|
| β-actin BT forward primer 65: (SEQ ID NO: 18) | 5' GTGTTTGTTTTTTTGATTAGGTGTTTAAGA 3' |
| β-actin BT reverse primer 65: (SEQ ID NO: 19) | 5' CTTTACACCAACCTCATAACCTTATC 3' |
| β-actin BT probe (Arm 3 underlined): (SEQ ID NO: 20 | 5' GACGCGGAGATAGTGTTGTGG/3C6/ 3' |
| Arm 3 QUASAR-670 FRET cassette (SEQ ID NO: 21) | 5'Q670/TCT/BHQ_2/AGCCGGTTTTCCGGCTGAGACTCCGCGTC/3C6 |
| Arm 5 FAM FRET cassette (SEQ ID NO: 22) | 5'd-FAM-TCT-BHQ-1-AGCCGGTTTTCCGGCTGAGACGTCCGTGG-C6 |
| Arm 7 FAM FRET cassette (SEQ ID NO: 24) | 5'd-FAM-TCT-BHQ-1-AGCCGGTTTTCCGGCTGAGAGGACGCGC-C6 |

FIG. 6

| | Name of Sequence | Sequence (5' to 3') |
|---|---|---|
| SEQ ID NO:1 | Danio rerio Ras association (RalGDS/AF-6) domain family 1 (rassf1) | tcagcaaatgaagtctgctctccgttcgctcctcaaagtaggacagatcgcgccggattaagcgttaatctgagtcttct<br>gcgcatgcgcatgaacgcgcgctacaagcggacaaggtgcgcgttcgaagaagaaacgaaccgagccggtttcgagc<br>agcgacaacgcgaatgaagcccacggagtaccgaaaccttgaggaattcatctttctgccagcggaggactgttttcag<br>tttagttttgagcgtaatggaagatgtttgggcacttttgcgcaatccctcatgttatcgcctcacagacacgcgtcgcgc<br>gcgcagattacgcttaatttgagcggatttgaggaaacagacgcgtttactgtcagtcgaggctctactgaagactgaa<br>agtggcttgtttgggtttaagattgacccagatgctactgaaaactgtcaatcaagaaggaaactcttgaagcaataaa<br>aacatcatctctgttatatgaagactgtcagatccacacagtgatccatgtttgtggatatgcaaacacatcagaacgag<br>acgctaaatttatcagcttgctttggagtaaacagcgttgctttaaaacactccacagtcataaatcatctccagccctaa<br>ccatggtccactgagccatgccgttcatcctcccacgatcccaaaatggcaaaatgtgagctcatcgagttgcaggactt<br>gactccgaatgaccgtattgagctggcacccccctagtgtccctccacccaccgtggtgcccactctggacaggtggagc<br>agagggaaggtggtgcgcatggtgggcgagcgcgtgcgcctggaggaccccgattggctgacgtgtaaaccaggacg<br>aggacatgactttcagccctgcagccagacacagctgagctggtgtgacctgtgtggagagttcatctggggcctgtac<br>agacagagcctccgctgcacacactgtaactacacttgtcactaccgctgtcaacccttcattcagctggactgcagctc<br>caacaccgacactatctgcgaacaatcaaactacagcgaggacaccatcgagacagacaccaatgtggatgagcagt<br>ctgaagtggactggaggaaacaggatctgtctgtcactgaaatacagcagaaagtgaaggaatacaatgctcaggtc<br>aacagtaacctcttcatggttctgaatcgtgacggctcatacactggcttcatcaaggtccagtttaagctggcgcgacc<br>cgtgtctcttcctcctccccgcagcgtctcctcctcctccatctcctcctcttgtttaggatgggatggcggctgtcaggagc<br>gaacttccttctacctgcccagagacacagtcaagcacctgcacatcagctccagcacccgtgccagagaggtcatcca<br>ggccctgctcaacaagttcactgtggtggacaatccggctaaatattccctgtatgagcgcagccagcgggacaatcaa<br>gtgtacttaaggaagttagctgatgatgaatgtccacttttcctgcgtctgtgtgctggacccaatgagaaagtcctgagt<br>ttagtgcttaaagagaatgaaaccggggaagtgaattgggatgcgttcagttttcctgaactccagaacttcctgcggat<br>tctccagcgggaggaagaagatcacgtccggcaaatcatacgccgatacactctggctcgtgataagatgaaagaggc<br>tatgaagaacttcagcaagcctggctgaatgaatctgtgtttatacctcacaaacaagagagatcgaggaggaaacaa<br>ggcttattactgtctgagtccaaagagtgtgtgaaagagcccttcgtcctactgtggacataatgagggttgaaagtgaa<br>atgcagtgagcgagagaagagatgcgtgtgtttgaagcatgactgttgagtgtgacttcacactggaggaaatgctgcg<br>ctcgtagccgtagatccagtggagagatgtcttcctgtggagaatctatatatcagtgcagattacagagtattttcagc<br>accatttaaacttgtcataggaaattaaacgaggattattttaatatctgtatcaaaatgccacctgttagtgacacagta<br>acttgtcatattttgaagctcccatgtatatatttggatgtttgttgtcaattattctgaaaatagatacaaataaactattt<br>ttccctttaaaatga |

FIG. 6 cont'd

| | Name of Sequence | Sequence (5' to 3') |
|---|---|---|
| SEQ ID NO:2 | Untreated Danio RASSF1 target (Fig. 1) | ATCAGAACGAGACGCTAAATTTATCAGCTTGCTTTGGAGTAAACAGCGTTGCTTTAAAACA<br>CTCCACAGTCATAAATCATCTCCAGCCCTAACCATGGTCCACTGAGCCATGCCGTTCATCCT<br>CCCACGATCCCAAAATGGCAAAATGTGAGCTCATCGAGTTGCAGGACTTGACTCCGAATGA<br>CCGTATTGAGCTGGCACCCCCTAGTGTCCCTCCACCCACCGTGGTGCCCACTCTGGACAGG<br>TGGAGCAGAGGGAAGGTGGTGCGCATGGTGGGCGAGCGCGTGCGCCTGGAGGACCCCG<br>ATTGGCTGACGTGTAAACCAGGACGAGGACATGACTTTCAGCCCTGCAGCCAGACACAGC<br>TGAGCTGGTGTGACCTGTGTGGAGAGTTCATCTGGGGCCTGTACAGACAGAGCCTCC |
| SEQ ID NO:3 | Bisulfite-treated Danio RASSF1 target (Fig. 1) | ATTAGAACGAGACGTTAAATTTATTAGTTTGTTTTGGAGTAAATAGCGTTGTTTTAAAATAT<br>TTTATAGTTATAAATTATTTTTAGTTTTAATTATGGTTTATTGAGTTATGTCGTTTATTTTTTT<br>ACGATTTTAAAATGGTAAAATGTGAGTTTATCGAGTTGTAGGATTTGATTTCGAATGATCG<br>TATTGAGTTGGTATTTTTTAGTGTTTTTTTATTTATCGTGGTGTTTATTTTGGATAGGTGGAG<br>TAGAGGGAAGGTGGTGCGTATGGTGGGCGAGCGCGTGCGTTTGGAGGATTTCGATTGGT<br>TGACGTGTAAATTAGGACGAGGATATGATTTTTAGTTTTGTAGTTAGATATAGTTGAGTTG<br>GTGTGATTTGTGTGGAGAGTTTATTTGGGGTTTGTATAGATAGAGTTTTC |
| SEQ ID NO:4 | ZF_RASSF1 UT forward primer | CGCATGGTGGGCGAG |
| SEQ ID NO:5 | ZF_RASSF1 UT reverse primer | ACACGTCAGCCAATCGGG |
| SEQ ID NO:6 | ZF_RASSF1 UT Probe (Arm 3) | GACGCGGAGGCGCGTGCGCC/3C6/ |
| SEQ ID NO:7 | ZF_RASSF1 BT forward primer | TGCGTATGGTGGGCGAG |
| SEQ ID NO:8 | ZF_RASSF1 BT reverse primer | CCTAATTTACACGTCAACCAATCGAA |
| SEQ ID NO:9 | ZF_RASSF1 BT probe (Arm 3) | GACGCGGAGGCGCGTGCGTTT/3C6/ |
| SEQ ID NO:10 | ZF_RASSF1 BT probe (Arm 5) | CCACGGACGGCGCGTGCGTTT/3C6/ |
| SEQ ID NO:11 | Synthetic Zebrafish RASSF1 sense strand (Fig. 2) | TCCAC/iMe-dC/GTGGTGCCCACTCTGGACAGGTGGAGCAGAGGGAAGGTGGTG/iMe-<br>dC/GCATGGTGGG/iMe-dC/GAG/iMe-dC/G/iMe-dC/GTG/iMe-<br>dC/GCCTGGAGGACCC/iMe-dC/GATTGGCTGA/iMe-dC/GTGTAAACCAGGA/iMe-<br>dC/GAGGACATGACTTTCAGCCCTGCAGCCAGACACAGCTGAGCTGGTGTGACCTGTGTGG<br>AGAGTTCATCTGG |
| SEQ ID NO:12 | Synthetic Zebrafish RASSF1 antisense strand (Fig. 2) | CCAGATGAACTCTCCACACAGGTCACACCAGCTCAGCTGTGTCTGGCTGCAGGGCTGAAAG<br>TCATGTCCT/iMe-dC/GTCCTGGTTTACA/iMe-dC/GTCAGCCAAT/iMe- |

FIG. 6 cont'd

| | Name of Sequence | Sequence (5' to 3') |
|---|---|---|
| | | dC/GGGGTCCTCCAGG/iMe-dC/GCA/iMe-dC/G/iMe-dC/GCT/iMe-dC/GCCCACCATG/iMe-dC/GCACCACCTTCCCTCTGCTCCACCTGTCCAGAGTGGGCACCA/iMe-dC/GGTGGA |
| SEQ ID NO:13 | Untreated β-actin Target | CTCTGACCTGAGTCTCCTTTGGAACTCTGCAGGTTCTATTTGCTTTTTCCCAGATGAGCTCTT TTTCTGGTGTTTGTCTCTCTGACTAGGTGTCTAAGACAGTGTTGTGGGTGTAGGTACTAACA CTGGCTCGTGTGACAAGGCCATGAGGCTGGTGTAAAGCGGCCTTGGAGTGTGTATTAAGT AGGTGCACAGTAGGTCTGAACAGACTCCCCATCCCAAGA |
| SEQ ID NO:14 | Bisulfite treated β-actin Target | TTTTGATTTGAGTTTTTTTTGGAATTTTGTAGGTTTTATTTGTTTTTTTTTAGATGAGTTTTTTT TTTGGTGTTTGTTTTTTTGATTAGGTGTTTAAGATAGTGTTGTGGGTGTAGGTATTAATATT GGTTTGTGTGATAAGGTTATGAGGTTGGTGTAAAGTGGTTTTGGAGTGTGTATTAAGTAG GTGTATAGTAGGTTTGAATAGATTTTTTATTTTAAGA |
| SEQ ID NO:15 | β-actin UT forward primer | CCATGAGGCTGGTGTAAAG |
| SEQ ID NO:16 | β-actin UT reverse primer | CTACTGTGCACCTACTTAATACAC |
| SEQ ID NO:17 | β-actin UT Probe (Arm 1 ) | CGCCGAGGGCGGCCTTGGAG/3C6/ |
| SEQ ID NO:18 | β-actin BT forward primer 65 | GTGTTTGTTTTTTTGATTAGGTGTTTAAGA |
| SEQ ID NO:19 | β-actin BT reverse primer 65 | CTTTACACCAACCTCATAACCTTATC |
| SEQ ID NO:20 | β-actin BT probe (Arm 3) | GACGCGGAGATAGTGTTGTGG/3C6/ |
| SEQ ID NO:21 | Arm 3 QUASAR-670 FRET cassette | Q670/TCT/BHQ_2/AGCCGGTTTTCCGGCTGAGACTCCGCGTC/3C6 |
| SEQ ID NO:22 | Arm 5 FAM FRET cassette | d-FAM-TCT-BHQ-1-AGCCGGTTTTCCGGCTGAGACGTCCGTGG-C6 |

NUCLEIC ACID CONTROL MOLECULES FROM NON-HUMAN ORGANISMS

CROSS-REFERENCE TO RELATED APPLICATIONS

The present application is a continuation of U.S. patent application Ser. No. 17/529,896, filed Nov. 18, 2021, now U.S. Pat. No. 11,952,615, which is a divisional of U.S. patent application Ser. No. 16/318,578, filed Jan. 17, 2019, now U.S. Pat. No. 11,208,680, which is a § 371 U.S. National Entry Application of PCT/US2017/042842, filed Jul. 19, 2017, which claims the priority benefit of U.S. Provisional Patent Application 62/364,049, filed Jul. 19, 2016, each of which is incorporated by reference in its entirety.

SEQUENCE LISTING

The text of the computer readable sequence listing filed herewith, titled "34545-404_SEQUENCE_LISTING", created Feb. 27, 2024, having a file size of 25,902 bytes, is hereby incorporated by reference in its entirety.

FIELD

The present invention provides DNA compositions that find use as controls in DNA processing and in nucleic acid testing methods. In particular, provided herein are DNA compositions for use as control molecules in human DNA processing and testing, e.g., of mutations and/or methylation of DNA isolated from human samples.

BACKGROUND

Nucleic acids from human samples that are analyzed for the presence of mutations and/or for methylation status associated with disease or risk of disease typically pass through a number of process steps during analysis. These steps may comprise, e.g., filtration, precipitation, capture, washing, elution, and/or chemical modification. For analysis of DNA sequences [or just "DNA"] to determine methylation status, processing typically comprises treatment with bisulfite to covert unmethylated dC bases to dU residues, which makes them more readily distinguishable from the methyl-C residues that are protected from bisulfite conversion.

Sample processing steps can be evaluated for efficiency and efficacy by the use of control DNAs of known composition. For example, nucleic acid extraction from bodily fluids often requires the addition of an exogenous nucleic acid as a process control that can be measured post-extraction to assess the efficiency of the process and be able to determine success or failure modes.

The nature of the process control nucleic acid used is usually dependent on the assay type and the material that is being measured. For example, if the assay being used is for detection and/or quantification of double stranded DNA or mutations in it, then double stranded DNA process controls are typically spiked into the samples pre-extraction. Similarly, for assays that monitor mRNA or microRNAs, the process controls used are typically either RNA transcripts or synthetic microRNA.

With process controls, assays are configured for the detection and quantification of both the process control, to assess the efficiency of the extraction process, and the analyte of interest. If the signal from the process control meets the assay specifications for recovery (e.g., a cutoff for percentage of added material recovered after processing), then the analyte-specific signal is considered valid and calls are then made. Alternatively, if the signal from the process control is outside the specifications for recovery, then the analyte-specific signal is considered invalid.

Typically, the process control material is selected to resemble the type of nucleic acid being assayed. If one is testing a combination DNA, RNA, methylated-DNA, and microRNA, then individual process controls need to be used for each type of assay. For example, for DNA testing (mutation detection or DNA quantification), plasmid or synthetic DNA with similar % GC content to that of the analyte being tested are usually employed, and for mRNA testing and quantification, transcript RNAs of similar % GC are also used. Some also use Armored RNA technology, in which the RNA process controls are packaged into the coat protein of *Escherichia coli* bacteriophage MS2, which prevents RNA degradation from RNases. Armored RNA process controls are usually used for assays that target viral RNAs such as HIV and HCV. For microRNA testing and quantification, exogenous microRNAs from different species than the one being tested are typically used. For example, microRNAs native to *C. elegans* are sometimes used as exogenous controls for human microRNA testing.

For methylated DNA (meDNA) testing in which the meDNA undergoes bisulfite treatment prior to detection and quantification, it is desirable to have a control molecule that is also methylated such that both extraction and bisulfite conversion processes can be verified, but that does not share any cross-reacting sequences with DNA from a sample to be analyzed, e.g., a sample from a human subject.

SUMMARY

The present invention provides nucleic acids from non-human species that have features similar to human nucleic acids (e.g., percent methylation of DNA) and that undergo normal testing and processing to control and provide a normal range of results for human nucleic acid detection assays. Further, these non-human nucleic acids have sequences not found in human nucleic acids and therefore provide control nucleic acids that do not cross-react with detection assays designed to detect human nucleic acid target molecules.

These non-human controls are referred to as run controls and they serve as indicators for assay performance and validity at each process step. The run controls also provide insights into assay performance, making it possible to detect, e.g., operator, systematic, and/or instrumentation errors. The run control nucleic acids provided herein find use as targets that undergo the entire assay process, e.g., from isolation/capture, to bisulfite conversion, through setup, reaction, and detection assay.

In some embodiments the technology provides compositions comprising a synthetic methylated DNA that has no significant homology to mammalian DNA, and that is in a mixture with mammalian DNA. In some embodiments, the mixture comprises additional components, e.g., an oligonucleotide comprising a region complementary to the synthetic methylated DNA; and oligonucleotide comprising a region complementary to the mammalian DNA; a bacterial, phage, viral, archaeal, or non-fish eukaryotic nucleic acid polymerase; and/or a bacterial, phage, archaeal, or non-fish eukaryotic DNA modifying enzyme. In certain embodiments, the synthetic methylated DNA comprises zebrafish DNA. In preferred embodiments, the zebrafish DNA comprises at least a portion of the zebrafish rassf1 gene. In particularly preferred embodiments, the synthetic methylated DNA comprises at least a portion of SEQ ID NO: 1 or its complement, preferably SEQ ID NO:2 or its complement.

In some embodiments, the composition comprises DNA that has been treated with a bisulfite reagent, and the synthetic methylated DNA has been converted with bisulfite reagent as described hereinbelow. In preferred embodiments, the converted synthetic DNA comprises at least a portion of SEQ ID NO:3 or its complement.

Some embodiments of the technology provide a composition comprising isolated methylated zebrafish DNA and a second component in a mixture, wherein said second component is selected from non-fish DNA; a non-fish eukaryotic cell; and/or a non-fish biological sample. In some embodiments the non-fish DNA is mammalian, preferably human. Similarly, in some embodiments, the non-fish eukaryotic cell is mammalian, and in preferred embodiments, it is human. In some embodiments, the non-fish biological sample is mammalian, and in preferred embodiments, it is human. In particularly preferred embodiments the biological sample from a human comprises one or more of blood, serum, plasma, tissue, stool, or sputum.

In preferred embodiments, the zebrafish DNA is synthetic. As described above, in preferred embodiments, the zebrafish DNA comprises at least a portion of the zebrafish rassf1 gene, preferably at least a portion of SEQ ID NO: 1 or its complement, preferably SEQ ID NO:2 or its complement. In some embodiments the DNA is bisulfite-treated and comprises at least a portion of SEQ ID NO:3 or its complement.

The compositions described above may comprise further components. For example, one or more of the mixtures described above may comprise a bacterial, phage, viral, archaeal, or non-fish eukaryotic nucleic acid polymerase and/or a bacterial, phage, archaeal, or non-fish eukaryotic DNA modifying enzyme. In some embodiments the nucleic acid polymerase is a DNA polymerase and in preferred embodiments, it is a thermostable DNA polymerase, e.g., Taq DNA polymerase, as described in detail in the hereinbelow. In some embodiments, the DNA modifying enzyme comprises a ligase, an exonuclease, and/or an endonuclease. In preferred embodiments, the endonuclease is a flap endonuclease, e.g., a FEN-1 endonuclease. In particularly preferred embodiments, the FEN-1 endonuclease is from a thermophilic archaeal organism.

In preferred embodiments, the methylated zebrafish DNA is synthetic and comprises an oligonucleotide having the sequence of SEQ ID NO:11 and/or an oligonucleotide having the sequence of SEQ ID NO:12, as shown in FIG. 6, which can anneal to form a double-stranded segment of synthetic methylated zebrafish DNA.

The technology further provides methods of treating samples. For example, in some embodiments the technology provides a method of treating a sample containing DNA from a subject that is not a zebrafish, comprising a) combining isolated methylated zebrafish DNA with the sample in a mixture; and b) treating said mixture to purify DNA from said mixture to produce, e.g., a DNA sample that comprises both the non-zebrafish DNA and the methylated zebrafish DNA.

In other embodiments, the method comprises treating a sample containing DNA from a mammal, comprising a) combining a synthetic methylated DNA having no significant homology to mammalian DNA with the DNA from a mammal, in a mixture; and b) treating the mixture to purify DNA from the mixture, to produce, e.g., a DNA sample that comprises both the mammalian DNA and the synthetic methylated DNA.

The technology is not limited to any particular method of purifying or isolating DNA from the mixtures described above. For example, in some embodiments, a method as described above comprises binding DNA to a support, preferably silica or silica-coated particle, e.g., in the presence of a chaotrope. In some embodiments, the method further comprises treating the DNA purified from the mixture with a bisulfite reagent. In preferree embodiments, the method further comprises detecting DNA purified from the mixture with a nucleic acid detection assay, e.g., a polymerase chain reaction, a QuARTS flap assay, etc.

In preferred embodiments, the nucleic acid detection assay comprises detecting both DNA from a cell or sample (e.g., mammalian DNA) and either methylated zebrafish DNA or methylated DNA that has no significant homology to mammalian DNA.

As described above, in preferred embodiments, zebrafish DNA comprises at least a portion of the zebrafish rassf1 gene, preferably at least a portion of SEQ ID NO:1 or its complement, preferably SEQ ID NO:2 or its complement. In some embodiments the DNA is bisulfite-treated and comprises at least a portion of SEQ ID NO:3 or its complement.

The technology further contemplates kits for providing or producing compositions and/or for conducting methods described above. For example, in some embodiments, a kit comprises isolated methylated zebrafish DNA and/or a synthetic methylated DNA having no significant homology to mammalian DNA and an additional component, including but not limited to, e.g., an oligonucleotide such as a primer or probe complementary to a non-fish target DNA, e.g., a mammalian DNA, a bisulfite reagent, a silica or silica-coated particle, a chaotropic agent (e.g., guanidine isothiocyanate, guanidine hydrochloride), a buffer, a nucleic acid polymerase and/or a DNA modifying enzyme, a FRET cassette, etc. In preferred embodiments, wherein the synthetic methylated DNA comprises at least a portion of SEQ ID NO: 1 or its complement or SEQ ID NO:2 or its complement.

In some embodiments, the synthetic methylated DNA comprises an oligonucleotide having the sequence of SEQ ID NO:11 and/or an oligonucleotide having the sequence of SEQ ID NO: 12, and in certain preferred embodiments, both oligonucleotides are provided together, and at least some of the complementary strands are annealed together.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 1 shows a target segment of the rassf1 gene of zebrafish (*Danio rerio*). The DNA sequence is shown in untreated form (UT), having the natural DNA sequence, and in a calculated bisulfite-treated form (BT), in which each cytosine that is not within a CpG dinucleotide is converted to a T nucleotide. Assay oligonucleotides suitable for amplification and flap endonuclease assay detection of the untreated and bisulfite-treated target sequences are also shown.

FIG. 2 depicts oligonucleotides having complementary sequences derived from rassf1 gene of *Danio rerio*. "iMe-dC" represents internal methylated cytosine and in the sequences shown, each CpG locus has a methylated cytosine. The sense and antisense oligonucleotides may be annealed to form a double-stranded segment of rassf1, as described in Example 2.

FIG. 5 shows a target segment of the human β-actin gene. The DNA sequence is shown in untreated form (UT), having the natural sequence, and in a calculated bisulfite-treated form (BT), in which each cytosine that is not within a CpG dinucleotide is converted to a T nucleotide. Assay oligonucleotides suitable for amplification and flap endonuclease assay detection of the untreated and bisulfite-treated target sequences are also shown.

FIG. 6 shows a table of nucleic acid sequences described herein.

DEFINITIONS

Figure 3:
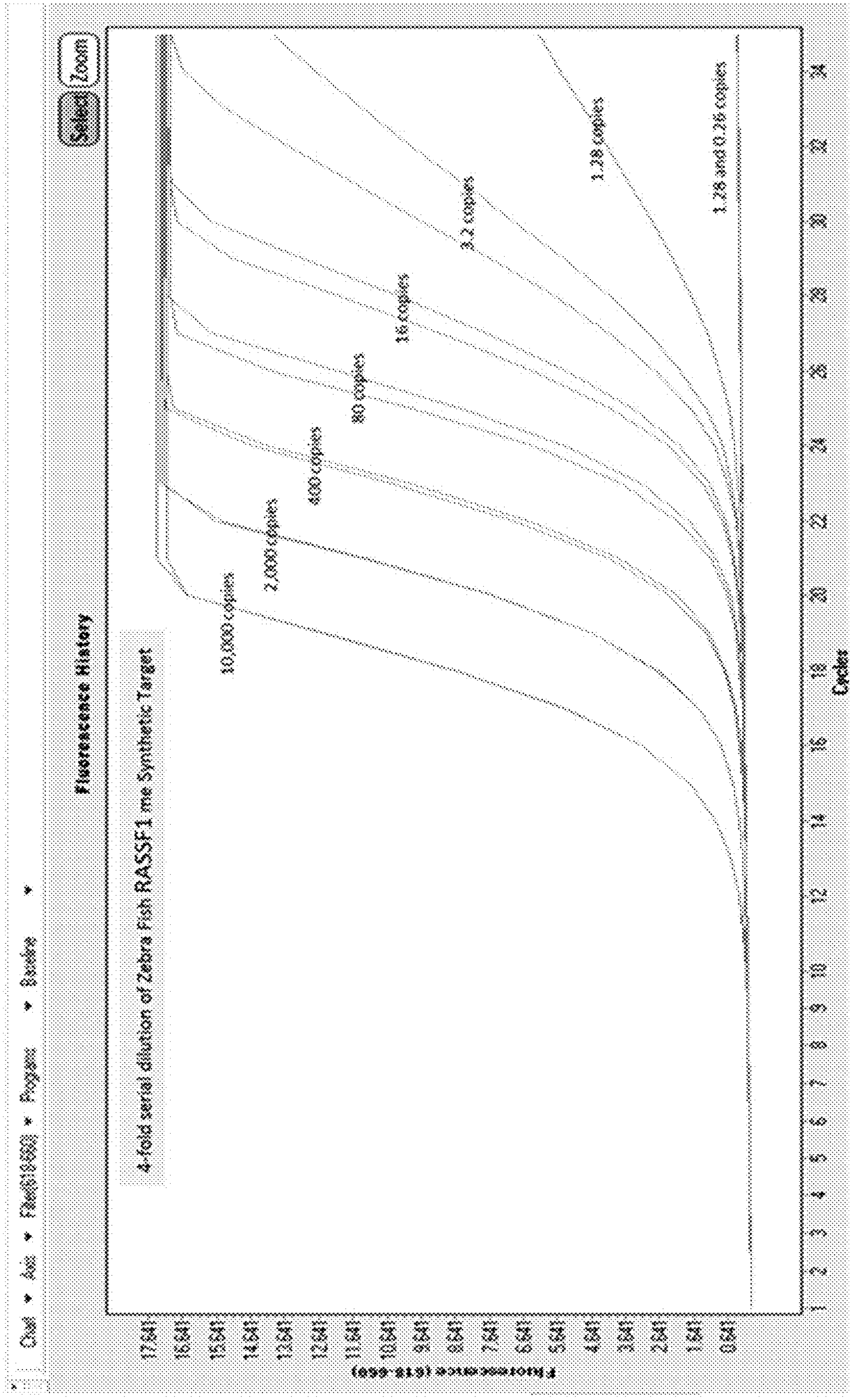
FIG. 3 show a graph comparing fluorescence signal produced using serial dilutions of the synthetic zebrafish DNA shown in FIG. 2 in quantitative amplification reactions, as described in Example 2.

To facilitate an understanding of the present technology, a number of terms and phrases are defined below. Additional definitions are set forth throughout the detailed description.

The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

As used herein, "a" or "an" or "the" can mean one or more than one. For example, "a" widget can mean one widget or a plurality of widgets.

The transitional phrase "consisting essentially of" as used in claims in the present application limits the scope of a claim to the specified materials or steps "and those that do not materially affect the basic and novel characteristic(s)" of the claimed invention, as discussed in In re Herz, 537 F.2d 549, 551-52, 190 USPQ 461, 463 (CCPA 1976). For example, a composition "consisting essentially of" recited elements may contain an unrecited contaminant at a level such that, though present, the contaminant does not alter the function of the recited composition as compared to a pure composition, i.e., a composition "consisting of" the recited components.

As used herein, the term "analyte" is to be construed broadly as any compound, molecule, element, ion, or other substance of interest to be detected, identified, or characterized.

As used herein, the terms "patient" or "subject" refer to organisms to be subject to various tests provided by the technology, wherein the organism or subject is not a zebrafish. The term "subject" includes animals, preferably mammals, including humans. In a preferred embodiment, the subject is a primate. In an even more preferred embodiment, the subject is a human. Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject' includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; pinnipeds; and horses. Thus, also provided is the diagnosis and treatment of livestock, including, but not limited to, domesticated swine, ruminants, ungulates, horses (including race horses), and the like. The presently-disclosed subject matter further includes a system for diagnosing a lung cancer in a subject. The system can be provided, for example, as a commercial kit that can be used to screen for a risk of lung cancer or diagnose a lung cancer in a subject from whom a biological sample has been collected. An exemplary system provided in accordance with the present technology includes assessing the methylation state of a marker described herein.

The term "sample" as used herein is used in its broadest sense. For example, a sample relates to a material or mixture of materials, typically, although not necessarily, in liquid form, containing one or more analytes of interest. A sample may be obtained from a biological, environmental, or synthetic source. In particular embodiments, a sample is suspected of containing a human gene or chromosome or sequences (e.g., fragments) associated with a human chromosome. Samples may comprise a cell, chromosomes isolated from a cell (e.g., a spread of metaphase chromosomes), genomic DNA (e.g., in solution or bound to a solid support), RNA (e.g., in solution or bound to a solid support), cDNA (e.g., in solution or bound to a solid support), and the like. A sample may contain contaminants (e.g., non-target nucleic acid, proteins, small molecules, biological or environmental matter, etc.) or may be in a purified or semi-purified form.

The term "target," when used in reference to a nucleic acid detection or analysis method herein, refers to a nucleic acid having a particular sequence of nucleotides to be detected or analyzed, e.g., in a sample or reaction mixture suspected of containing the target nucleic acid. In some embodiments, a target is a nucleic acid having a particular non-wild-type sequence (e.g., a mutant sequence (e.g., a point mutation relative to wild-type)) or a sequence for which it is desirable to determine a methylation status. When used in reference to the polymerase chain reaction, "target" generally refers to the region of nucleic acid bounded by the primers used for polymerase chain reaction. Thus, the "target" is sought to be sorted out from other nucleic acid sequences that may be present in a sample. A "target amplicon" is a nucleic acid generated by amplification (e.g., PCR amplification) of a target sequence. The term "sample template" refers to nucleic acid originating from a sample that is analyzed for the presence of a target.

The term "control" as used herein refers to nucleic acid having known features (e.g., known sequence (e.g., wild-type, mutant, allele, etc.), known concentration, known formulation, known modification (e.g., methylation) for use in comparison to an experimental target (e.g., a nucleic acid of unknown sequence (e.g., wild-type, mutant, allele, etc.), unknown concentration, unknown formulation, unknown modification (e.g., methylation)).

As used herein, the term "locus" refers to a particular position (e.g., of a mutation, polymorphism, or a C residue in a CpG dinucleotide, etc.) within a defined region or segment of a nucleic acid, such as a gene or any other characterized sequence on a chromosome or RNA molecule. A locus is not limited to any particular size or length and may refer to a portion of a chromosome, a gene, a functional genetic element, or a single nucleotide or base pair. As used herein in reference to CpG sites that may be methylated, a locus refers to the C residue in the CpG dinucleotide. As used herein in reference to a position that may be mutated (e.g., KRAS G35T, etc.), a locus refers to the nucleotide (or nucleotides) or base pair (or base pairs) that may either be in wild-type or mutant form.

As used herein, “methylation” or “methylated,” as used in reference to the methylation status of a cytosine, e.g., in a CpG dinucleotide locus, generally refers to the presence or absence of a methyl group at position 5 of the cytosine residue (i.e., indicating whether a particular cytosine is 5-methylcytosine). Methylation may be determined directly, e.g., as evidenced by routine methods for analysis of the methylation status of cytosines, e.g., by determining the sensitivity (or lack thereof) of a particular C-residue to conversion to uracil by treatment with bisulfite. For example, a cytosine residue in a sample that is not converted to uracil when the sample is treated with bisulfite in a manner that would be expected to convert that residue if non-methylated (e.g., under conditions in which a majority or all of the non-methylated cytosines in the sample are converted to uracils) may generally be deemed “methylated.”

As used herein, a nucleic acid having a methylation percentage of 100% indicates that the nucleic acid has a methyl group attached to the C of every CpG dinucleotide, e.g., the nucleic acid is “fully methylated”. In addition, as used herein in some contexts, 100% methylation indicates that all instances and/or copies of a particular nucleic acid are fully methylated, e.g., each instance and/or copy of the nucleic acid has a methyl group attached to the C of every CpG dinucleotide. It is to be understood that experimental and/or other reaction conditions for producing a nucleic acid having 100% methylation may, in some embodiments, produce a nucleic acid that has substantially 100% methylation, e.g., an amount of methylation that is lower than 100% and/or approximately 100%, e.g., 90%, 91%, 92%, 93%, 94%, 95%, 96%, 97, 98%, 99%, 99.5%, or 99.9% methylation, either in the extent of methylation of the CpG dinucleotides of each nucleic acid strand and/or in the number of instances and/or copies of each nucleic acid that have 100% methylation.

As used herein, a “methylation-specific reagent” refers to a reagent that modifies a nucleotide of the nucleic acid molecule as a function of the methylation state of the nucleic acid molecule, or a methylation-specific reagent, refers to a compound or composition or other agent that can change the nucleotide sequence of a nucleic acid molecule in a manner that reflects the methylation state of the nucleic acid molecule. Methods of treating a nucleic acid molecule with such a reagent can include contacting the nucleic acid molecule with the reagent, coupled with additional steps, if desired, to accomplish the desired change of nucleotide sequence. Such methods can be applied in a manner in which unmethylated nucleotides (e.g., each unmethylated cytosine) is modified to a different nucleotide. For example, in some embodiments, such a reagent can deaminate unmethylated cytosine nucleotides to produce deoxy uracil residues. An exemplary reagent is a bisulfite reagent.

The term “bisulfite reagent” refers to a reagent comprising bisulfite, disulfite, hydrogen sulfite, or combinations thereof, useful as disclosed herein to distinguish between methylated and unmethylated CpG dinucleotide sequences. Methods of said treatment are known in the art (e.g., PCT/EP2004/011715 and WO 2013/116375, each of which is incorporated by reference in its entirety). In some embodiments, bisulfite treatment is conducted in the presence of denaturing solvents such as but not limited to n-alkylenglycol or diethylene glycol dimethyl ether (DME), or in the presence of dioxane or dioxane derivatives. In some embodiments the denaturing solvents are used in concentrations between 1% and 35% (v/v). In some embodiments, the bisulfite reaction is carried out in the presence of scavengers such as but not limited to chromane derivatives, e.g., 6-hydroxy-2,5,7,8,-tetramethylchromane 2-carboxylic acid or trihydroxybenzone acid and derivates thereof, e.g., Gallic acid (see: PCT/EP2004/011715, which is incorporated by reference in its entirety). In certain preferred embodiments, the bisulfite reaction comprises treatment with ammonium hydrogen sulfite, e.g., as described in WO 2013/116375.

A change in the nucleic acid nucleotide sequence by a methylation-specific reagent can also result in a nucleic acid molecule in which each methylated nucleotide is modified to a different nucleotide.

The term “methylation assay” refers to any assay for determining the methylation state of one or more CpG dinucleotide sequences within a sequence of a nucleic acid.

As used herein, “sensitivity” as used in reference to a diagnostic assay, e.g., a methylation assay, refers to clinical sensitivity. Clinical sensitivity refers to the proportion of positive samples that give a positive result using a diagnostic assay. Sensitivity is generally calculated as the number of true positives identified by the assay divided by the sum of the number of true positives and the number of false negatives determined by the assay on known positive samples. Similarly, the term “specificity” refers to the proportion or number of true negatives determined by the assay divided by the sum of the number of true negatives and the number of false positives determined by the assay on known negative sample(s).

The term “wild-type” refers to a gene, gene product, or fragment thereof that has the characteristics of that gene or gene product when isolated from a naturally occurring source and is of the sequence and/or form that is most frequently observed in a population. In contrast, the terms “modified,” “mutant,” and/or “variant” refer to a gene, gene product, or a fragment thereof that displays modifications in sequence and or functional properties (i.e., altered characteristics) when compared to wild-type. It is noted that naturally occurring mutants can be isolated; these are identified by the fact that they have altered characteristics when compared to the wild-type gene or gene product.

The term “neoplasm” as used herein refers to any new and abnormal growth of tissue. Thus, a neoplasm can be a premalignant neoplasm or a malignant neoplasm.

The term “neoplasm-specific marker,” as used herein, refers to any biological material or element that can be used to indicate the presence of a neoplasm. Examples of biological materials include, without limitation, nucleic acids, polypeptides, carbohydrates, fatty acids, cellular components (e.g., cell membranes and mitochondria), and whole cells. In some instances, markers are particular nucleic acid regions (e.g., genes, intragenic regions, specific loci, etc.). Regions of nucleic acid that are markers may be referred to, e.g., as “marker genes,” “marker regions,” “marker sequences,” “marker loci,” etc.

The term “primer” refers to an oligonucleotide, whether occurring naturally as, e.g., a nucleic acid fragment from a restriction digest, or produced synthetically, that is capable of acting as a point of initiation of synthesis when placed under conditions in which synthesis of a primer extension product that is complementary to a nucleic acid template strand is induced, (e.g., in the presence of nucleotides and an inducing agent such as a DNA polymerase, and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label. When used in reference to flap assay, the term refers to an oligonucleotide that interacts with a target nucleic acid to form a cleavage structure in the presence of an invasive oligonucleotide. As used in reference to a flap assay, the terms "flap probe" and "flap oligonucleotide" are used interchangeably.

The term "target," as used herein refers to a nucleic acid sought to be sorted out from other nucleic acids, e.g., by probe binding, amplification, isolation, capture, etc. For example, when used in reference to the polymerase chain reaction, "target" refers to the region of nucleic acid bounded by the primers used for polymerase chain reaction, while when used in an assay in which target DNA is not amplified, e.g., in some embodiments of an invasive cleavage assay, a target comprises the site at which a probe and invasive oligonucleotides (e.g., INVADER oligonucleotide) bind to form an invasive cleavage structure, such that the presence of the target nucleic acid can be detected. A "segment" is defined as a region of nucleic acid within the target sequence.

The term "marker", as used herein, refers to a substance (e.g., a nucleic acid, or a region of a nucleic acid, or a protein) that may be used to distinguish non-normal cells (e.g., cancer cells) from normal cells, e.g., based on presence, absence, or status (e.g., methylation state) of the marker substance.

As used herein the term "fish DNA" is distinct from zebrafish DNA and refers to exogenous non-target DNA isolated from fish. The term "exogenous" as used in reference to non-target DNA refers to non-target DNA that is isolated and purified from a source other than the source or sample containing the target DNA. Such exogenous DNA is selected to be undetected by an assay configured to detect and/or quantify the target nucleic acid in the reaction to which the exogenous DNA is added. For example, purified fish DNA is exogenous DNA with respect to a sample comprising human target DNA, e.g., as described in U.S. Pat. No. 9,212,392, which is incorporated herein by reference. Bulk purified fish DNA is commercially available, e.g., provided in the form of cod and/or herring sperm DNA (Roche Applied Science, Mannheim, Germany) or salmon DNA (USB/Affymetrix).

As used herein, the term "zebrafish DNA" is distinct from fish DNA and refers to DNA isolated from *Danio rerio*, or created in vitro (e.g., enzymatically, synthetically) to have a sequence of nucleotides found in DNA from *Danio rerio*. In preferred embodiments, the zebrafish DNA is a methylated DNA added as a detectable control DNA, e.g., a process control for verifying DNA recovery through sample processing steps.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specific PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons." Those of skill in the art will understand the term "PCR" encompasses many variants of the originally described method using, e.g., real time PCR, nested PCR, reverse transcription PCR (RT-PCR), single primer and arbitrarily primed PCR, etc.

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, (Hologic, Inc.) and are described, e.g., in U.S. Pat. Nos. 5,846,717, 5,985,557, 5,994,069, 6,001,567, 6,090,543, and 6,872,816; Lyamichev et al., Nat. Biotech., 17:292 (1999), Hall et al., PNAS, USA, 97:8272 (2000), and US 2009/0253142, each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction (PCR), described above; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Baranay Proc. Natl. Acad. Sci USA 88, 189-93 (1991)); and sandwich hybridization methods (e.g., U.S. Pat. No. 5,288,609, herein incorporated by reference in its entirety).

In some embodiments, target nucleic acid is amplified (e.g., by PCR) and amplified nucleic acid is detected simultaneously using an invasive cleavage assay. Assays configured for performing a detection assay (e.g., invasive cleavage assay) in combination with an amplification assay are described in U.S. Pat. No. 9,096,893, incorporated herein by reference in its entirety for all purposes. Additional amplification-plus-invasive cleavage detection configurations, termed the QuARTS method, are described in, e.g., in U.S. Pat. Nos. 8,361,720; 8,715,937; 8,916,344; and 9,212,392, each of which is incorporated herein by reference for all purposes. The term "invasive cleavage structure" as used herein refers to a cleavage structure comprising i) a target nucleic acid, ii) an upstream nucleic acid (e.g., an invasive or "INVADER" oligonucleotide), and iii) a downstream nucleic acid (e.g., a probe), where the upstream and downstream nucleic acids anneal to contiguous regions of the target nucleic acid, and where an overlap forms between the a 3' portion of the upstream nucleic acid and duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, e.g., as disclosed, for example, in U.S. Pat. No. 6,090,543, incorporated herein by reference in its entirety. In some embodiments, one or more of the nucleic acids may be attached to each other, e.g., through a covalent linkage such as nucleic acid stem-loop, or through a non-nucleic acid chemical linkage (e.g., a multi-carbon chain). As used herein, the term "flap endonuclease assay" includes "INVADER" invasive cleavage assays and QuARTS assays, as described above.

The term "invasive oligonucleotide" refers to an oligonucleotide that hybridizes to a target nucleic acid at a location adjacent to the region of hybridization between a probe and the target nucleic acid, wherein the 3' end of the invasive oligonucleotide comprises a portion (e.g., a chemical moiety, or one or more nucleotides) that overlaps with the region of hybridization between the probe and target. The 3' terminal nucleotide of the invasive oligonucleotide may or may not base pair a nucleotide in the target. In some embodiments, the invasive oligonucleotide contains sequences at its 3' end that are substantially the same as sequences located at the 5' end of a portion of the probe oligonucleotide that anneals to the target strand.

The term "flap endonuclease" or "FEN," as used herein, refers to a class of nucleolytic enzymes, typically 5' nucleases, that act as structure-specific endonucleases on DNA structures with a duplex containing a single stranded 5' overhang, or flap, on one of the strands that is displaced by another strand of nucleic acid (e.g., such that there are overlapping nucleotides at the junction between the single and double-stranded DNA). FENs catalyze hydrolytic cleavage of the phosphodiester bond at the junction of single and double stranded DNA, releasing the overhang, or the flap.

Flap endonucleases are reviewed by Ceska and Savers (Trends Biochem. Sci. 1998 23:331-336) and Liu et al (Annu. Rev. Biochem. 2004 73: 589-615; herein incorporated by reference in its entirety). FENs may be individual enzymes, multi-subunit enzymes, or may exist as an activity of another enzyme or protein complex (e.g., a DNA polymerase).

A flap endonuclease may be thermostable. For example, FEN-1 flap endonuclease from archaeal thermophilic organisms are typical thermostable. As used herein, the term “FEN-1” refers to a non-polymerase flap endonuclease from a eukaryote or archaeal organism. See, e.g., WO 02/070755, and Kaiser M. W., et al. (1999) J. Biol. Chem., 274:21387, which are incorporated by reference herein in their entireties for all purposes.

As used herein, the term “cleaved flap” refers to a single-stranded oligonucleotide that is a cleavage product of a flap assay.

The term “cassette,” when used in reference to a flap cleavage reaction, refers to an oligonucleotide or combination of oligonucleotides configured to generate a detectable signal in response to cleavage of a flap or probe oligonucleotide, e.g., in a primary or first cleavage structure formed in a flap cleavage assay. In preferred embodiments, the cassette hybridizes to a non-target cleavage product produced by cleavage of a flap oligonucleotide to form a second overlapping cleavage structure, such that the cassette can then be cleaved by the same enzyme, e.g., a FEN-1 endonuclease.

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label, e.g., a fluorophore. In particularly preferred embodiments, a cassette comprises labeled moieties that produce a FRET effect.

As used herein, the term “FRET” refers to fluorescence resonance energy transfer, a process in which moieties (e.g., fluorophores) transfer energy e.g., among themselves, or, from a fluorophore to a non-fluorophore (e.g., a quencher molecule). In some circumstances, FRET involves an excited donor fluorophore transferring energy to a lower-energy acceptor fluorophore via a short-range (e.g., about 10 nm or less) dipole-dipole interaction. In other circumstances, FRET involves a loss of fluorescence energy from a donor and an increase in fluorescence in an acceptor fluorophore. In still other forms of FRET, energy can be exchanged from an excited donor fluorophore to a non-fluorescing molecule (e.g., a “dark” quenching molecule). FRET is known to those of skill in the art and has been described (See, e.g., Stryer et al., 1978, Ann. Rev. Biochem., 47:819; Selvin, 1995, Methods Enzymol., 246:300; Orpana, 2004 Biomol Eng 21, 45-50; Olivier, 2005 Mutant Res 573, 103-110, each of which is incorporated herein by reference in its entirety).

In an exemplary flap detection assay, an invasive oligonucleotide and flap oligonucleotide are hybridized to a target nucleic acid to produce a first complex having an overlap as described above. An unpaired “flap” or “arm” is included on the 5' end of the flap oligonucleotide. The first complex is a substrate for a flap endonuclease, e.g., a FEN-1 endonuclease, which cleaves the flap oligonucleotide to release the 5' flap portion. In a secondary reaction, the released 5' flap product serves as an invasive oligonucleotide on a FRET cassette to again create the structure recognized by the flap endonuclease, such that the FRET cassette is cleaved. When the fluorophore and the quencher are separated by cleavage of the FRET cassette, a detectable fluorescent signal above background fluorescence is produced.

The term “real time” as used herein in refers to detection of nucleic acid amplification or signal amplification by the detection or measurement of the accumulation of products or signal in the reaction while the reaction is in progress, e.g., during incubation or thermal cycling. Such detection or measurement may occur continuously, or it may occur at a plurality of discrete points during the progress of the amplification reaction, or it may be a combination. For example, in a polymerase chain reaction, detection (e.g., of fluorescence) may occur continuously during all or part of thermal cycling, or it may occur transiently, at one or more points during one or more cycles. In some embodiments, real time detection of PCR or QuARTS reactions is accomplished by determining a level of fluorescence at the same point (e.g., a time point in the cycle, or temperature step in the cycle) in each of a plurality of cycles, or in every cycle. Real time detection of amplification may also be referred to as detection “during” the amplification reaction.

As used herein, the term “quantitative amplification data set” refers to the data obtained during quantitative amplification of the target sample, e.g., target DNA. In the case of quantitative PCR or QuARTS assays, the quantitative amplification data set is a collection of fluorescence values obtained during amplification, e.g., during a plurality of, or all of the thermal cycles. Data for quantitative amplification is not limited to data collected at any particular point in a reaction, and fluorescence may be measured at a discrete point in each cycle or continuously throughout each cycle.

The abbreviations “Ct” and “Cp” as used herein, in reference to data collected during real time PCR and PCR+INVADER assays, refer to the cycle at which signal (e.g., fluorescent signal) crosses a predetermined threshold value indicative of positive signal. Various methods have been used to calculate the threshold that is used as a determinant of signal verses concentration, and the value is generally expressed as either the “crossing threshold” (Ct) or the “crossing point” (Cp). Either Cp values or Ct values may be used in embodiments of the methods presented herein for analysis of real-time signal for the determination of the percentage of variant and/or non-variant constituents in an assay or sample.

As used herein, the term “kit” refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term “fragmented kit” refers to delivery systems comprising two or more separate containers that each contain a subportion of the total kit components. The containers may be delivered to the intended recipient together or separately. For example, a first container may contain an enzyme for use in an assay, while a second container contains oligonucleotides.

The term “system” as used herein refers to a collection of articles for use for a particular purpose. In some embodiments, the articles comprise instructions for use, as information supplied on e.g., an article, on paper, or on recordable media (e.g., DVD, CD, flash drive, etc.). In some embodiments, instructions direct a user to an online location, e.g., a website.

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, percentage methylation, allele frequencies, RNA expression levels, protein expression, phenotypes correlating to genotypes, etc. "Allele frequency information" refers to facts or data pertaining to allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc.

DETAILED DESCRIPTION OF THE INVENTION

The present invention provides nucleic acids from non-human species that have features similar to human nucleic acids (e.g., microRNAs, percent methylation of DNA) that undergo normal testing and processing to control and provide a normal range of results for human nucleic acid detection assays. Further, these non-human nucleic acids have sequences not found in human nucleic acids and therefore provide control nucleic acids that do not cross-react nor interfere with detection assays designed to detect human nucleic acid target molecules.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

The technology disclosed herein provides nucleic acid, e.g., DNA, methylated DNA and microRNA, from non-mammalian organisms, e.g., honey bees (*Apis mellifera*) and zebrafish (*Danio rerio*). In some embodiments, the nucleic acids are isolated from these organisms, while in other embodiments, nucleic acids are isolated from cultured cells derived from these organisms. In yet other embodiments, the nucleic acids are synthetic copies of nucleic acids found in these organisms. In yet other embodiments, these nucleic acids are synthetic copies of nucleic acids found in these organisms as they would be if treated with a bisulfite reagent.

In some preferred embodiments, nucleic acids are from zebrafish (*Danio rerio*). Zebrafish display high degrees of methylation in certain genes or genic regions, e.g., rassf1, tert, c-jun, c-myca (see, e.g., Fang, et al., Comp Biochem Physiol B Biochem Mol Biol 166:99-108 (2013)). The genes rassf1 and tert have particularly low homology with human nucleic acid sequences. For example, computer-assisted comparison of rassf1 using the BLAST program shows only a handful of sequence alignments, all of about 27 or fewer bases, when compared against human DNA.

The technology provides synthetic nucleic acids produced from sequence information from non-human organisms. For example, in some embodiments, the technology provides synthetic double-stranded methylated DNA. "Target" refers to a nucleic acid or a gene (a "gene target") comprising portions, loci, regions, etc. having sequences and/or methylation status(es) that is/are to be detected or measured during a detection assay. In some types of samples, e.g., blood, plasma, and stool samples, DNA is usually found as fragments comprising 100 to 1000 bp (e.g., 100 to 500, e.g., 100 to 200, e.g., 150 bp), the regions of the nucleic acids that are to be detected or measured during a sample-based assay are usually found in fragments of the targeted nucleic acids. Accordingly, as used herein, "fragment", "target fragment", or "target gene fragment" refers to a DNA of 100 to 1000 bp (e.g., 100 to 500, e.g., 100 to 200, e.g., 150 bp) comprising the portions, loci, regions, etc. having sequences and/or methylation status(es) that is/are to be detected or measured during a detection assay in embodiments of the technology directed to assessing DNA of that size (e.g., a stool sample and/or fecal matter-based assay for colorectal cancer). As used in embodiments of a run control described herein, the fragments may be isolated from a natural source or the fragments may be synthetic. For instance, some embodiments provide synthetic oligonucleotides of 100 to 500 bp (e.g., 100 to 250, e.g., 100 to 200, e.g., 150 bp) comprising portions of gene targets (e.g., target fragments) that are used to calibrate, control, validate, assess, evaluate, etc. an assay for measuring and/or detecting gene targets associated with a disease state, e.g., colorectal cancer (e.g., an assay for assessing the sequence and/or methylation status of gene targets in a sample obtained from a subject who is being tested for the presence of colorectal cancer). The fragments may also be recombinant and/or semi-synthetic, e.g., comprising natural and synthesized portions.

In some embodiments, a nucleic acid comprises a wild-type sequence and in some embodiments, a nucleic acid comprises a mutant sequence. In some embodiments, a nucleic acid comprises one or more methylated cytosines (me-C) and in some embodiments, a nucleic acid comprises one or more non-methylated cytosines (C). Preferred embodiments provide nucleic acids having defined sequences (e.g., wild-type and mutant sequences) and/or defined methylation patterns (e.g., cytosine bases within the nucleic acid are methylated or non-methylated according to a defined pattern or sequence). For example, in some embodiments, 100% of the molecules in a mixture have the same pattern of partial methylation of cytosines. In some embodiments, every cytosine within every CpG dinucleotide within a single nucleic acid molecule has a methyl group attached (e.g., 100% methylation of a nucleic acid molecule). In some embodiments related to methylated nucleic acids, each (e.g., every one) of the individual nucleic acid molecules produced according to a defined methylation pattern have the defined sequence and/or methylation pattern (e.g., 100% methylation of all nucleic acid molecules). In some embodiments related to 100% methylation of a nucleic acid molecule or of each molecule in a collection of molecules, the methylation is substantially, effectively, or essentially 100%, e.g., the sample is treated as and/or behaves as a sample having 100% methylation regardless of the actual exact state of methylation, e.g., methylation that may be less than 100% in actuality. In other embodiments, strands having different methylation patterns (e.g., 100% methylated, unmethylated, or a particular pattern of methylated and unmethylated sites) are mixed in defined amounts to produce a run control having pre-defined proportions and patterns of methylation at one or more CpG dinucleotides in a control sequence. In particularly preferred embodiments, a run control is synthesized to exhibit 100% methylation CpG dinucleotides within the sequence.

In preferred embodiments, the run control comprises nucleic acid that is double-stranded, e.g., as provided by annealing two complementary synthetic oligonucleotides. In some embodiments, the controls are produced according to a process as follows (and as described in Example 2): DNA (e.g., single stranded DNA) is synthesized according to the sequence and methyl-C positions desired. DNA synthesis is provided, e.g., by an automated DNA synthesizer and stock solutions of the four standard A, T, C, and G bases and a stock solution of 5'-methyl-C. Then, in some embodiments the single-stranded oligonucleotides are annealed (e.g., by mixing, heating (e.g., melting), and cooling, for example, at a controlled rate, in an appropriate buffer) to provide natural-like double-stranded targets. Then, in some embodiments, control formulations (e.g., a DNA control reagent) are produced by mixing the double stranded targets at the desired concentrations to produce the desired signal (e.g., see above) in a buffer (e.g., 80% DNA Stabilization Buffer (500 mM Tris, 150 mM EDTA, and 10 mM NaCl, pH 9) with or without fish DNA in the diluent.

The technology is not limited in the buffer that finds use to produce the control. For example, the buffer may be HEPES, PIPES, SSC, MES, MOPS, phosphate buffer, citric acid (citrate) based buffers, other Tris buffers, etc. and may have any suitable pH (typically from 5.5 to 10).

In some embodiments, the run control comprises nucleic acid that is derived from a plasmid. For example, in some embodiments, run control fragments are cloned into a plasmid vector. In some embodiments, the vector comprises the sequence of a plasmid vector (e.g., a pUC plasmid, etc.) and one or more run control fragments, e.g., linked in series (e.g., directly or separated by linkers) and separated by restriction sites, e.g., as described in co-pending application Ser. No. 15/033,803, PCT/US14/71460, and Ser. No. 15/105,178 which are incorporated herein by reference. In some embodiments, the run control is methylated in vitro, e.g., using a methylase enzyme.

In some embodiments, run control fragments are used to evaluate, calibrate, assess, and/or validate extraction procedures for target DNAs from samples and/or for assays for the identification, detection, and/or characterization of disease, a pre-disease state, or susceptibility to disease in a subject (e.g., human).

Run controls such as zebrafish DNA are selected to mimic target nucleic acids to be extracted from samples for analysis, e.g., disease marker DNA from biological specimen, such that the run control can be added to the sample and carried through all steps of extraction, bisulfite conversion, and nucleic acid detection in parallel with the target DNA.

In some embodiments, the run control comprises synthetic DNA fragments and a buffer. For example, in some embodiments, the run control comprises DNA Stabilization Buffer (500 mM Tris, 150 mM EDTA, and 10 mM NaCl, pH 9), e.g., 50% to 100% (e.g., 55%, 60%, 65%, 70%, 75%, 80%, 85%, 90%, 95% DNA Stabilization Buffer) and fish DNA (e.g., fish (e.g., salmon) sperm DNA, as described in U.S. Pat. No. 9,212,392, incorporated herein by reference, e.g., at 10 to 100 ng/ml, e.g., 20 to 80 ng/ml, e.g., 30 to 60 ng/ml, e.g., 50 ng/mL).

In some embodiments, run controls are provided in multiples of the concentrations used in the control reactions, e.g., to provide a concentrated stock solution (e.g., 2×, 3×, 4×, 5×, 10×, 20×, 25×, 50×, 100×, 1000×) of a run control that is diluted (e.g., with a buffer) before use. In some embodiments, run controls are provided as a reagent in a kit, e.g., for purifying and/or bisulfite treating and/or detecting a target nucleic acid, e.g. a methylated human DNA.

In some embodiments, an exemplary assay utilizing a run control of the present invention proceeds as follows. A run control is added to a sample from a biological or environmental source (e.g., a sample of body fluid) and nucleic acid is then extracted from the sample. In some embodiments, nucleic acid is processed with a binding reagent (e.g., a silica magnetic particle) to concentrate, isolate, and/or purify the nucleic acid from non-nucleic acid substances. In some embodiments, the sample and/or the nucleic acid containing the added run control is isolated from the biological or environmental source (e.g., a stool sample) is treated with an inhibitor removal reagent, either before or after capture with the capture reagent.

In some embodiments, the isolated sample nucleic acid with added run control is treated with a bisulfite reagent to convert non-methylated cytosines to uracils. In some embodiments, the run control composition comprises synthetic nucleic acids that are methylated such that the efficacy of conversion with bisulfite can be monitored.

In some embodiments, the extracted nucleic acid comprising the added run control is assayed, e.g., by a QuARTS assay. The run control and the isolated nucleic acid are subject to the same reaction and assay conditions (e.g., amplification conditions), and the results of the reactions are detected, e.g., in real time, for both the target and run control. Then, the results of the assay with the run control are assessed relative to the expected results for the run control (e.g., to determine if the run control results are within a pre-defined acceptable range) to provide an indicator that the assay testing the target nucleic acid from the biological sample is valid or is not valid, to assess assay performance, user error, instrumentation errors, reagent quality, etc.

Processing the run controls in the same manner as the test sample (e.g., the nucleic acid from the biological, environmental, etc. sample) provides for assessing the performance of the procedures and assays on the test sample and thus provides information about the validity and/or confidence in the assay results.

In certain embodiments, the nucleic acid isolated from the patient sample and/or the run controls are added to a reaction mixture (reaction mix), e.g., for PCR and/or QuARTs assay. Typically, these reaction mixtures contain reagents for polymerase chain reaction (PCR) amplification, although reaction mixtures for other methods of amplification and/or analysis are within the scope of the present invention. In some embodiments, reaction mixtures comprise PCR reagents for amplifying a nucleic acid target sequence. The reaction mixtures employed in the method may therefore comprise: one or more pairs of primers, a suitable PCR buffer (e.g., pH buffered, comprising salt (e.g., KCl) and a source of divalent cation (e.g., $MgCl_2$), etc.), deoxynucleoside triphosphates (e.g., dGTP, dATP, dTTP, and dCTP), and a thermostable DNA polymerase. Depending on the application, the reaction mixture may also comprise additional components for further analysis, manipulation, and/or detection of polynucleotides or target sequences therein, e.g., invasive oligonucleotide(s), flap oligonucleotide(s), flap endonuclease (e.g., thermostable FEN-1), FRET cassette(s), etc.

The exact identities and concentrations of the reagents present in the reaction mixture may be similar to or the same as those employed in the field. In some embodiments, a reaction mixture contains $Mg^{2+}$ at a concentration of between about 1.8 mM and 3 mM, 4 mM to 10 mM, 6 mM to 9 mM, etc. Exemplary reaction buffers and DNA polymerases that may be employed in the subject reaction mixture include those described in various publications (e.g., Ausubel, et al., Short Protocols in Molecular Biology, 3rd ed., Wiley & Sons 1995; Sambrook et al., Molecular Cloning: A Laboratory Manual, Third Edition, 2001 Cold Spring Harbor, N.Y.; herein incorporated by reference in their entireties). Reaction buffers and DNA polymerases suitable for PCR may be purchased from a variety of suppliers, e.g., Invitrogen (Carlsbad, Calif.), Qiagen (Valencia, Calif.), and Stratagene (La Jolla, Calif.). Exemplary polymerases include Taq, Pfu, Pwo, UlTma, and Vent, and variants thereof, although many other polymerases may be employed in certain embodiments. Exemplary flap endonucleases include Afu FEN-1, Pfu FEN-1 and Ave FEN-1 (See, e.g., WO 02/070755, and Kaiser M. W., et al. (1999) J. Biol. Chem., 274:21387).

Guidance for the reaction components suitable for use with a polymerase and suitable conditions for their use is found in the literature supplied with the polymerase. Primer design is described in a variety of publications (e.g., Diffenbach and Dveksler, PCR Primer, A Laboratory Manual, Cold Spring Harbor Press 1995; R. Rapley, The Nucleic Acid Protocols Handbook (2000), Humana Press, Totowa, N.J.; Schena and Kwok et al., Nucl. Acid Res. 1990 18:999-1005; herein incorporated by reference in their entireties). Primer and probe design software programs are also commercially available, including without limitation, Primer Detective (ClonTech, Palo Alto, Calif.), Lasergene, (DNASTAR, Inc., Madison, Wis.), OLIGO (National Biosciences, Inc., Plymouth, Minn.), and iOligo (Caesar Software, Portsmouth, N.H.).

In particular embodiments, a reaction mix contains reagents for assaying multiple different target sequences in parallel (e.g., at least 2, 3, 4 . . . 10, or more). In these cases, the reaction mix may contain multiple pairs of PCR primers. In certain embodiments, the various oligonucleotides used in the method are designed so as not to interfere with one another. In a multiplex reaction, the primers may be designed to have similar thermodynamic properties (e.g., similar $T_m$s, G/C content, hairpin stability, and in certain embodiments may all be of a similar length (e.g., from 18 to 30 nt (e.g., 20 to 25 nt). In some embodiments, other reagents used in the reaction mixture are $T_m$ matched, to work under the same temperature(s) as other components, or during a selected subset of temperatures used, e.g., during a thermocycling reaction.

In some embodiments, the reaction mixture is present in a vessel, including without limitation, a tube; a multi-well plate (e.g., 96-well, 384-well, 1536-well), a microfluidic device, etc. In certain embodiments, multiple multiplex reactions are performed in the same reaction vessel. Depending on how the reaction is performed, the reaction mixture may be of any volume, e.g., 0.1 μl to 5 μl, 5 μl to 200 μl (e.g., 10 μl to 100 μl), although volumes outside of this range are envisioned.

In certain embodiments, a reaction mix comprises a nucleic acid (e.g., comprising a target sequence, from a biological sample, from an environmental sample, synthetic (e.g., from a run control), etc.). In particular embodiments, the mix comprises genomic DNA, fragments thereof, or an amplified version thereof (e.g., genomic DNA amplified using the methods of Lage et al, Genome Res. 2003 13: 294-307 or published patent application US 2004/0241658 both of which are herein incorporated by reference in their entireties), e.g., from a patient to be tested for a disease, e.g., colorectal cancer. In exemplary embodiments, the genomic sample may contain genomic DNA from a mammalian cell such a human, mouse, rat or monkey cell. The sample may be made from cultured cells or cells of a clinical sample (e.g., a tissue biopsy, scrape or lavage or cells of a forensic sample (i.e., cells of a sample collected at a crime scene), etc.).

In particular embodiments, a nucleic acid in a reaction mix is obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, pancreatic fluid, and semen. In particular embodiments, a sample may be obtained from a subject (e.g., a human) and it may be processed prior to use in the subject assay. For example, the nucleic acid may be extracted from the sample prior to use, methods for which are known. In some embodiments the DNA is treated with bisulfite prior to use in an assay, wherein unmethylated cytosine bases are converted to uracil bases.

In certain embodiments, a reaction mixture (e.g., comprising a nucleic acid from the patient; comprising a run control) comprises one or more reagents (e.g., oligonucleotides such as primers, flap probes, detection cassettes; enzymes such as polymerases; chemical reagents; etc.) for performing amplification, processing, manipulation, analysis, detection steps or assays (e.g., other than and/or in addition to PCR). The present invention is not limited by the scope of the nucleic acid analysis, manipulation, and/or detection methods with which it finds use.

In some embodiments, multiple different reaction mixes (e.g., at least one comprising a run control and at least one comprising a nucleic acid from a patient sample) are provided (e.g., for use in an experiment or assay). In some embodiments, multiple vessels (e.g., wells, tubes, channels, etc.) are provided, each containing a reaction mix (e.g., at least one comprising a run control and at least one comprising an experimental target nucleic acid).

In certain embodiments, the run control compositions, reaction mixtures, and/or methods described herein find use in a variety of diagnostic, medical, analytical, and research applications, and the invention should not be viewed as limited to any particular field or use. However, in particular embodiments, the present invention finds use in the analysis, detection, characterization, etc. of nucleic acid (e.g., human nucleic acid, target nucleic acid, etc.) from stool. Compositions, methods, devices, etc. for use in the embodiments described herein are found in, for example, U.S. Pat. Nos. 8,361,720; 7,981,612; 7,368,233; 6,964,846; 6,919,174; 6,849,403; 6,844,155; 6,818,404; 6,750,020; 6,586,177; 6,551,777; 6,503,718; 6,498,012; 6,482,595; 6,475,738; 6,428,964; 6,415,455; 6,406,857; 6,351,857; 6,303,304; 6,300,077; 6,280,947; 6,268,136; 6,203,993; 6,146,828; 6,143,529; 6,020,137; 5,952,178; 5,928,870; 5,888,778; 5,830,665; 5,741,650; 5,670,325; each of which is herein incorporated by reference in its entirety for any purpose. In certain embodiments, the compositions and methods described herein find use in, for example, a quantitative allele-specific real-time target and signal amplification assay (QuARTS assay), as described in, e.g., in U.S. Pat. Nos. 8,361,720; 8,715,937; 8,916,344; and 9,212,392.

EXPERIMENTAL

During the development of embodiments of technology related to tests for colorectal cancer, experiments suggested that including control DNA samples would provide an improved test. Accordingly, technologies are provided herein comprising DNA controls that generate specific signals when processed through a workflow in parallel with experimental (e.g., unknown) samples (e.g., from a patient). In particular, the controls provided herein comprise various nucleic acid targets that are captured during the capture process, converted during the bisulfite conversion, and present the correct sequence for detection by the QuARTS mutation and/or methylation assays.

Example 1

Sample Preparation Methods

Methods for DNA Isolation and QUARTS Assay

The following provides exemplary method for DNA isolation prior to analysis, and an exemplary QUARTS assay, such as may be used in accordance with embodiments of the technology. Application of QuARTS technology to DNA from blood and various tissue samples is described in this example, but the technology is readily applied to other nucleic acid samples, as shown in other examples.

DNA Isolation from Cells and Plasma

For cell lines, genomic DNA may be isolated from cell conditioned media using, for example, the "Maxwell® RSC ccfDNA Plasma Kit (Promega Corp., Madison, WI). Following the kit protocol, 1 mL of cell conditioned media (CCM) is used in place of plasma, and processed according to the kit procedure.

An alternative exemplary procedure for isolating DNA from plasma is as follows:

- To a 4 mL sample of plasma, 300 µL of Proteinase K (20 mg/mL) is added and mixed.
- Add 3 µL of 1 µg/µL of fish DNA diluent to the plasma-proteinase K mixture.
- Add 2 mL of plasma lysis buffer to plasma.
  - Plasma lysis buffer is:
    - 4.3M guanidine thiocyanate
    - 10% IGEPAL CA-630 (Octylphenoxy poly(ethyleneoxy)ethanol, branched)
    - (5.3 g of IGEPAL CA-630 combined with 45 mL of 4.8 M guanidine thiocyanate)
- Incubate mixtures at 55° C. for 1 hour with shaking at 500 rpm.
- Add 3 mL of plasma lysis buffer and mix.
- Add 200 µL magnetic silica binding beads (16 µg of beads/µL} and mix again.
- Add 2 mL of 100% isopropanol and mix.
- Incubate at 30° C. for 30 minutes with shaking at 500 rpm.
- Place tube(s) on magnet and let the beads collect. Aspirate and discard the supernatant.
- Add 750 µL GuHCl-EtOH to vessel containing the binding beads and mix.
  - GuHCl-EtOH wash buffer is:
    - 3M GuHCl (guanidine hydrochloride)
    - 57% EtOH (ethyl alcohol)
- Shake at 400 rpm for 1 minute.
- Transfer samples to a deep well plate or 2 mL microcentrifuge tubes.
- Place tubes on magnet and let the beads collect for 10 minutes. Aspirate and discard the supernatant.
- Add 1000 µL wash buffer (10 mM Tris HCl, 80% EtOH) to the beads, and incubate at 30° C. for 3 minutes with shaking.
- Place tubes on magnet and let the beads collect. Aspirate and discard the supernatant.
- Add 500 µL wash buffer to the beads and incubate at 30° C. for 3 minutes with shaking.
- Place tubes on magnet and let the beads collect. Aspirate and discard the supernatant.
- Add 250 µL wash buffer and incubate at 30° C. for 3 minutes with shaking.
- Place tubes on magnet and let the beads collect. Aspirate and discard the remaining buffer.
- Add 250 µL wash buffer and incubate at 30° C. for 3 minutes with shaking.
- Place tubes on magnet and let the beads collect. Aspirate and discard the remaining buffer
- Dry the beads at 70° C. for 15 minutes, with shaking.
- Add 125 µL elution buffer (10 mM Tris HCl, pH 8.0, 0.1 mM EDTA) to the beads and incubate at 65° C. for 25 minutes with shaking.
- Place tubes on magnet and let the beads collect for 10 minutes.
- Aspirate and transfer the supernatant containing the DNA to a new vessel or tube.

Zebrafish DNA, e.g., natural, or synthetic DNA prepared as described in Example 2, may be added to the plasma sample as described herein. For example, 100 µL of 120 copies per µL synthetic zebrafish DNA (see Example 2) in 0.4 ng/µL of fish DNA diluent (bulk genomic DNA isolated from salmon, cod and/or herring, as described, e.g., in U.S. Pat. No. 9,212,392) may be added prior to addition of the plasma lysis buffer, before or after the addition of Proteinase K and fish DNA.

Bisulfite Conversion of DNA

DNA for methylation testing is treated with bisulfite using, e.g., the EZ-96 DNA Methylation Kit (Zymo Research, Irvine CA) or using ammonium hydrogen sulfite as described in U.S. Pat. No. 9,315,853 and in U.S. Prov. Patent Appl. No. 62/249,097, each of which is incorporated herein by reference in its entirety.

An exemplary method of treating DNA with a bisulfite reagent to convert unmethylated cytosine residues is as follow:

I. Sulfonation of DNA Using Ammonium Hydrogen Sulfite

1. In each tube, combine 64 µL DNA, 7 µL 1 N NaOH, and 9 µL of carrier solution containing 0.2 mg/mL BSA and 0.25 mg/mL of fish DNA.
2. Incubate at 42° C. for 20 minutes.
3. Add 120 µL of 45% ammonium hydrogen sulfite and incubate at 66° For 75 minutes.

4 Incubate at 4° C. for 10 minutes.

II. Desulfonation Using Magnetic Beads

Materials

Magnetic beads (Promega MagneSil Paramagnetic Particles, Promega catalogue number AS1050, 16 µg/µL).

Binding buffer: 6.5-7 M guanidine hydrochoride.

Post-conversion Wash buffer: 80% ethanol with 10 mM Tris HCl (pH 8.0).

Desulfonation buffer: 70% isopropyl alcohol, 0.1 N NaOH was selected for the desulfonation buffer.

Samples are mixed using any appropriate device or technology to mix or incubate samples at the temperatures and mixing speeds essentially as described below. For example, a Thermomixer (Eppendorf) can be used for the mixing or incubation of samples. An exemplary desulfonation is as follows:

1. Mix bead stock thoroughly by vortexing bottle for 1 minute.
2. Aliquot 50 μL of beads into a 2.0 mL tube (e.g., from USA Scientific).
3. Add 750 μL of binding buffer to the beads.
4. Add 150 μL of sulfonated DNA from step I.
5. Mix (e.g., 1000 RPM at 30° C. for 30 minutes).
6. Place tube on the magnet stand and leave in place for 5 minutes. With the tubes on the stand, remove and discard the supernatant.
7. Add 1,000 μL of wash buffer. Mix (e.g., 1000 RPM at 30° C. for 3 minutes).
8. Place tube on the magnet stand and leave in place for 5 minutes. With the tubes on the stand, remove and discard the supernatant.
9. Add 250 μL of wash buffer. Mix (e.g., 1000 RPM at 30° C. for 3 minutes).
10. Place tube on magnetic rack; remove and discard supernatant after 1 minute.
11. Add 200 μL of desulfonation buffer. Mix (e.g., 1000 RPM at 30° C. for 5 minutes).
12. Place tube on magnetic rack; remove and discard supernatant after 1 minute.
13. Add 250 μL of wash buffer. Mix (e.g., 1000 RPM at 30° C. for 3 minutes).
14. Place tube on magnetic rack; remove and discard supernatant after 1 minute.
15. Add 250 μL of wash buffer to the tube. Mix (e.g., 1000 RPM at 30° C. for 3 minutes).
16. Place tube on magnetic rack; remove and discard supernatant after 1 minute.
17. Incubate all tubes at 30° C. with the lid open for 15 minutes.
18. Remove tube from magnetic rack and add 70 μL of elution buffer directly to the beads.
19. Incubate the beads with elution-buffer (e.g., 1000 RPM at 40° C. for 45 minutes).

20 Place tubes on magnetic rack for about one minute; remove and save the supernatant.

The converted DNA is then used in pre-amplification and/or flap endonuclease assays, as described below.

QuARTS Flap Endonuclease Assay

The QuARTS technology combines a polymerase-based target DNA amplification process with an invasive cleavage-based signal amplification process. The technology is described, e.g., in U.S. Pat. Nos. 8,361,720; 8,715,937; 8,916,344; and 9,212,392, each of which is incorporated herein by reference. Fluorescence signal generated by the QuARTS reaction is monitored in a fashion similar to real-time PCR and permits quantitation of the amount of a target nucleic acid in a sample.

An exemplary QuARTS reaction typically comprises approximately 400-600 nmol/l (e.g., 500 nmol/l) of each primer and detection probe, approximately 100 nmol/l of the invasive oligonucleotide, approximately 600-700 nmol/l of each FRET cassette (FAM, e.g., as supplied commercially by Hologic, Inc.; HEX, e.g., as supplied commercially by BioSearch Technologies; and Quasar 670, e.g., as supplied commercially by BioSearch Technologies), 6.675 ng/μl FEN-1 endonuclease (e.g., Cleavase® 2.0, Hologic, Inc.), 1 unit Taq DNA polymerase in a 30 μl reaction volume (e.g., GoTaq® DNA polymerase, Promega Corp., Madison, WI), 10 mmol/l 3-(n-morpholino) propanesulfonic acid (MOPS), 7.5 mmol/l $MgCl_2$, and 250 μmol/l of each dNTP. Exemplary QuARTS cycling conditions are as shown in the table below. In some applications, analysis of the quantification cycle ($C_q$) provides a measure of the initial number of target DNA strands (e.g., copy number) in the sample.

| Stage | Temp/Time | # of Cycles |
|---|---|---|
| Denaturation | 95° C./3' | 1 |
| Amplification 1 | 95° C./20" | 10 |
| | 67° C./30" | |
| | 70° C./30" | |
| Amplification 2 | 95° C./20" | 37 |
| | 53° C./1' | |
| | 70° C./30" | |
| Cooling | 40° C./30" | 1 |

Multiplex Targeted Pre-Amplification of Large-Volume Bisulfite-Converted DNA

To pre-amplify most or all of the bisulfite treated DNA from an input sample, a large volume of the treated DNA may be used in a single, large-volume multiplex amplification reaction. For example, DNA is extracted from cell lines (e.g., DFCI032 cell line (adenocarcinoma); H1755 cell line (neuroendocrine), using, for example, the Maxwell Promega blood kit #AS1400, as described above. The DNA is bisulfite converted, e.g., as described above.

A pre-amplification is conducted, for example, in a reaction mixture containing 7.5 mM $MgCl_2$, 10 mM MOPS, 0.3 mM Tris-HCl, pH 8.0, 0.8 mM KCl, 0.1 μg/μL BSA, 0.0001% Tween-20, 0.0001% IGEPAL CA-630, 250 μM each dNTP, oligonucleotide primers, (e.g., for 12 targets, 12 primer pairs/24 primers, in equimolar amounts (including but not limited to the ranges of, e.g., 200-500 nM each primer), or with individual primer concentrations adjusted to balance amplification efficiencies of the different target regions), 0.025 units/μL HotStart GoTaq concentration, and 20 to 50% by volume of bisulfite-treated target DNA (e.g., 10 μL of target DNA into a 50 μL reaction mixture, or 50 μL of target DNA into a 125 μL reaction mixture). Thermal cycling times and temperatures are selected to be appropriate for the volume of the reaction and the amplification vessel. For example, the reactions may be cycled as follows

| Stage | Temp/Time | # of Cycles |
|---|---|---|
| Pre-incubation | 95° C./5' | 1 |
| Amplification 1 | 95° C./30" | 10 |
| | 64° C./30" | |
| | 72° C./30" | |
| Cooling | 4° C./Hold | 1 |

After thermal cycling, aliquots of the pre-amplification reaction (e.g., 10 μL) are diluted to 500 μL in 10 mM Tris-HCl pH8.0, 0.1 mM EDTA, with or without fish DNA. Aliquots of the diluted pre-amplified DNA (e.g., 10 μL) are used in a QuARTS PCR-flap assay, e.g., as described above. See also U.S. Patent Appl. Ser. No. 62/249,097, filed Oct. 30, 2015, which is incorporated herein by reference for all purposes.

Example 2

Synthetic Zebrafish DNA as an Internal Processing Control

Complementary strands of methylated zebrafish DNA were synthesized having the sequences as shown in FIG. 2 by standard, well known DNA synthesis methods such as phosphoramidite addition, incorporating internal methyl C bases as indicated in the Figure.

A. Resuspension and Annealing of Complementary Synthetic DNA Strands

1. Resuspension of synthetic strands
   - a. Prepare separate 1 µM concentration solutions of each of the oligonucleotides shown in FIG. 2, in 100 mM 10 mM Tris-HCl pH8.0, 0.1 mM EDTA.
   - b. Incubate tube in 37° C. dry bath for 30 minutes to fully dissolve the DNA.
   - c. Cool to room temp (5 minutes) and briefly vortex and centrifuge to collect contents to bottom of tube.
   - d. Maintain resuspended oligonucleotides on ice during use, or place at −20° C. for long term storage.
2. Make 10×Annealing Buffer:
   - e. Prepare a solution of 500 mM NaCl, 200 mM Tris-HCl pH 8.0, and 20 mM $MgCl_2$.
3. Anneal synthetic strands:
   - f. In a total volume of 100 µL, combine equimolar amounts of each of the single-stranded oligonucleotides in 1×annealing buffer, e.g., as shown in the table below:

| Component | Stock Conc. | Final Conc. (copies/µl in 1 ml final volume) | Volume added (µL) |
|---|---|---|---|
| Zebrafish rassf1 me synthetic Target Sense Strand | 1 µM | 1.0E+10 | 16.6 |
| Zebrafish rassf1 me synthetic Target Anti-Sense Strand | 1 µM | 1.0E+10 | 16.6 |
| Annealing Buffer | 10X | NA | 10.0 |
| Water | NA | NA | 56.8 |
| | | total vol. | 100.0 µL |

- g. Heat the annealing mixture to 98° C. for 13 minutes.
   - h. Remove the reaction tube from the heat block and spin down briefly to collect condensation to bottom of tube.
   - i. Incubate the reaction tube at room temp for 20 minutes.
   - j. Add 0.9 ml fish DNA diluent (20 ng/ml fish DNA in 10 mM Tris-HCl pH8.0, 0.1 mM EDTA) to adjust to the concentration of zebrafish DNA to $1.0\times10^{10}$ copies/µL of annealed, double-stranded synthetic zebrafish DNA in a carrier of genomic fish DNA carrier.
   - k. Dilute 10 µL of the $1.0\times10^{0}$ copies/µL stock to 1 ml with 10 mM Tris-HCl pH8.0, 0.1 mM EDTA buffer to make $1.0\times10^{8}$ copies/µL.
   - l. Dilute 10 µL of the $1.0\times10^{8}$ copies/µL stock to 1 ml with 10 mM Tris-HCl pH8.0, 0.1 mM EDTA buffer to make $1.0\times10^{6}$ copies/µL.
   - m. Store all stocks at −20° C.

B. Test of Annealed, Double-Stranded Methylated Zebrafish Rassf1 DNA as an Assay Target The annealed DNA was analyzed using a QuARTS flap assay to assess performance of the synthetic DNA in quantitative detection assays. The assays were conducted as follows:

1. Prepare 5-fold serial dilutions of the annealed zebrafish target DNA in a fish DNA diluent (20 ng/ml fish DNA in 10 mM Tris-HCl pH 8.0, 0.1 mM EDTA) to achieve final concentrations of: $1.0\times10^{3}$, 200, 40, 8, 1.6, 0.32, 0.064, 0.0128 copies of zebrafish DNA per µL.
2. Prepare a 10×Oligo Mix containing: forward and reverse primers each at 2 µM, probe and FRET cassettes each at 5 µM, and dNTPs at 250 µM each dNTP (See below for primer, probe and FRET cassette sequences)

"UT" primers and probes are designed to detect DNA that is untreated, i.e., that has not been converted by bisulfite treatment.

| Oligo | Sequence (5'-3') | SEQ ID NO: |
|---|---|---|
| ZF_RASSF1 UT forward primer | CGCATGGTGGGCGAG | 4 |
| ZF_RASSF1_UT reverse primer | ACACGTCAGCCAATCGGG | 5 |
| ZF_RASSF1_UT Probe (Arm 3) | GACGCGGAGGCGCGTGCGCC/3C6 | 6 |
| Arm 3 QUASAR-670 FRET cassette | Q670/TCT/BHQ_2/ AGCCGGTTTTCCGGCTGAGACTCCG CGTC/3C6 | 21 |

3. Prepare a 20× Enzyme Mix containing:

200 mM MOPS, pH 7.5, 150 mM MgCl2, 6.38 mM Tris-HCl, pH 8.0, 15.94 mM KCl, 2 µg/µL BSA, 0.16% Tween-20, 0.16% IGEPAL CA-630, 25% Glycerol, 146 ng/µL Cleavase 2.0, 1 unit/µL HotStart GoTaq polymerase.
4. Prepare a QuARTS flap assay master mix, as follows:

| Component | µL vol of stock to add per reaction | µL vol for 36 reactions |
|---|---|---|
| Water | 15.50 | 558 |
| 10X Oligo Mix | 3.00 | 108 |
| 20X Enzyme Mix | 1.50 | 54 |
| total volume master mix | 20.0 | 720 |

5. Aliquot 20 µL of QuARTS master mix into each well of a 96 well assay plate. Add 10 µL of diluted sample to the wells containing master mix.
6. Seal plate with optical seal and put into LightCycler 480 and run profile described below:

| Light Cycler Parameters | | | | |
|---|---|---|---|---|
| Select Quasar channel: 618-660 nm<br>QuARTS Reaction Cycle: | | | | |
| Stage | Temp/Time | Ramp Rate (° C. per second) | Number of Cycles | Signal Acquisition |
| Pre-incubation | 95° C./3' | 4.4 | 1 | none |
| Amplification 1 | 95° C./20" | 4.4 | 10 | none |
| | 63° C./30" | 2.2 | | none |
| | 70° C./30" | 4.4 | | none |
| Amplification 2 | 95° C./20" | 4.4 | 35 | none |
| | 53° C./1' | 2.2 | | single |
| | 70° C./30" | 4.4 | | none |
| Cooling | 40° C./30" | 2.2 | 1 | none |

Figure 4:
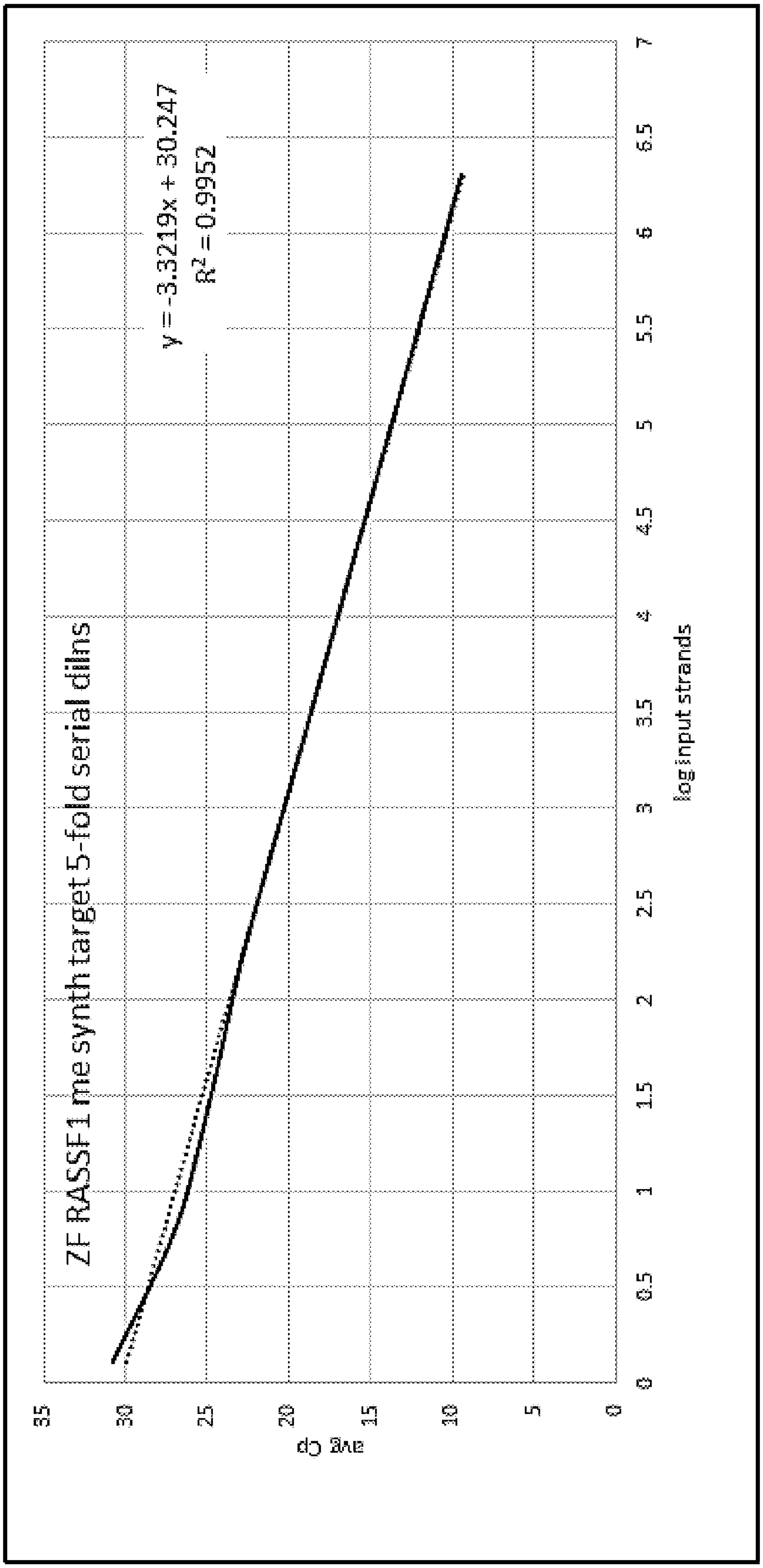
FIG. 4 compares the average Cp to log of input strands from the results shown in FIG. 3, as described in Example 2.

The results are shown in FIGS. 3-4, and show that standard curves of Cp vs log input strands (FIG. 4) shows a linear response down to 10 copies of zebrafish DNA per QuARTS assay reaction. These data also demonstrate that the zebrafish assay oligonucleotides do not cross-react with the carrier fish DNA used in the diluent.

Example 3

Assessment of Zebrafish DNA as a Process Control for DNA Extraction from Plasma and Treated with Bisulfite Following the serial dilution assay, an input strand value was chosen that would produce strand counts that fall within the range of the most commonly used calibrators. Calibrators for most QuARTS assays range from 200,000 strands per reaction down to 20 strands per reaction. It was calculated that adding 12,000 copies of synthetic zebrafish DNA (prepared as described above) to each plasma sample prior to extraction, and eluting the extracted DNA in a volume of 125 μL of buffer would result in 192 strands per μL of zebrafish DNA, and 1,920 strands per QuARTS assay based on 10 μL of sample per reaction.

To monitor consistency of extraction yields among the individual samples, 296 individual plasma samples were each spiked with 12,000 copies of zebrafish DNA prior to extraction. QuARTS flap assays as described in Example 1 and configured to detect both zebrafish DNA and β-actin were used to measure the number of copies of DNA recovered after processing and prior to bisulfite conversion.

A 70 μL aliquot of each of the extracted samples was then bisulfite-converted as described in Example 1, and 10 μL of bisulfite-treated DNA was tested in each QuARTS flap assay. The results across the 296 samples are shown below:

| Strands/rxn | Pre-bisulfite | Post-bisulfite |
|---|---|---|
| average | 557 | 60845 |
| Stan. Dev. | 111 | 8375 |
| CV | 20% | 14% |

These data show that the average strands detected both pre- and post-bisulfite treatment yield consistent and accurate zebrafish DNA strand counts, indicating that zebrafish DNA is consistent and reliable as a process control for both extraction and bisulfite conversion processes.

Example 4

Assessment of Cross-Reactivity Between Zebrafish DNA Detection Assays and Human DNA for Both Unconverted and Bisulfite-Treated Target DNAs This example looked at whether the zebrafish detection oligonucleotides cross-react with human DNA present in a reaction, and vice versa, both before and after bisulfite conversion (i.e., using zebrafish assay oligonucleotides directed to unconverted and bisulfite-converted zebrafish DNA). The assays were conducted as follows:

1. Extract DNA from 1 mL of human plasma using the Maxwell RSC ccfDNA Plasma Kit (Promega Corp., Madison, WI), in accordance with the manufacturer instructions. Add either 100 μL of zebrafish DNA as described in Example 2, to 120 copies/μL, or add 10 mM Tris-HCl, pH 8, 0.1 mM EDTA to the lysis buffer used in the extraction
2. Elute the DNA in 125 μL of 10 mM Tris-HCl pH8.0, 0.1 mM EDTA.
3. Perform QuARTS assay reactions in biplex using β-actin and zebrafish DNA assay on 10 μL of eluted DNA.

oligonucleotides for <u>un</u>treated DNAs, as shown below:

```
β-actin UT forward primer
                                        (SEQ ID NO: 15)
5' CCATGAGGCTGGTGTAAAG3'

β-actin UT reverse primer
                                        (SEQ ID NO: 16)
5' CTACTGTGCACCTACTTAATACAC3'

β-actin UT Probe (Arm 1 underlined)
                                        (SEQ ID NO: 17)
5' CGCCGAGGGCGGCCTTGGAG/3C6/

ZF_RASSF1 UT forward primer
                                         (SEQ ID NO: 4)
5'CGCATGGTGGGCGAG3'

ZF_RASSF1 UT reverse primer
                                         (SEQ ID NO: 5)
5'ACACGTCAGCCAATCGGG3'

Z_RASSF1 UT Probe (Arm 7 underlined)
                                        (SEQ ID NO: 23)
5'GCGCGTCCGCGCGTGCGCC/3C6/
```

The primer mixes for untreated target DNA comprised 200 nM each primer.

4. Perform bisulfite conversion on 70 μL of eluted DNA and elute converted in 70 μL of 10 mM Tris-HCl pH8.0, 0.1 mM EDTA;
5. Use 50 μL of bisulfite-converted DNA to perform biplex PCR using β-actin and zebrafish primers and probes directed to bisulfite-converted DNA, as follows:
   i. Prepare a mixture of the following primers oligonucleotides, each at a concentration of 750 nM

```
β-actin BT forward primer 65:
                                        (SEQ ID NO: 18)
5'GTGTTTGTTTTTTTGATTAGGTGTTTAAGA 3'

β-actin BT reverse primer 65:
                                        (SEQ ID NO: 19)
5'CTTTACACCAACCTCATAACCTTATC 3'
```

-continued

```
ZF_RASSF1 BT forward primer:
                                        (SEQ ID NO: 7)
5'TGCGTATGGTGGGCGAG3'

ZF_RASSF1 BT reverse primer:
                                        (SEQ ID NO: 8)
5'CCTAATTTACACGTCAACCAATCGAA3'
```

ii. For each bisulfite-treated sample, prepare the following PCR amplification reaction mixture:

| Reagent | Vol. per Rxn (μl) |
|---|---|
| Water | 9.625 |
| 10X reaction buffer | 7.5 |
| Primer Mix | 7.5 |
| Hotstart GoTaq (5 U/μL) | 0.375 |
| BST-treated DNA | 50 |

10×reaction buffer is 75 mM $MgCl_2$, 100 mM MOPS, 3 mM Tris-HCl, pH 8.0, 8 mM KCl, 1 μg/μL BSA, 0.001% Tween-20, and 0.001% IGEPAL CA-630.

iii. Perform 12 amplification cycles using the following cycling conditions:

| Stage | Temp/Time | #of Cycles |
|---|---|---|
| Pre-incubation | 95° C./5 min | 1 |
| Amplification | 95° C./30 s | 12 |
| | 64° C./60 s | |
| Cooling | 4° C./Hold | 1 |

iv. Dilute the reactions of step iii by combining 10 μL of amplified reaction product with 90 μL of 10 mM TrisHCl, pH 8.0, 0.1 mM EDTA.

v. Make a 10×oligonucleotide/dNTP mix containing dNTPs at 250 μM each and the oligonucleotides shown below, with the forward and reverse primers each at 2 μM, and the probe and FRET cassettes, each at 5 μM:

```
β-actin BT forward primer 65:
                                        (SEQ ID NO: 18)
5'GTGTTTGTTTTTTTGATTAGGTGTTTAAGA 3'

β-actin BT reverse primer 65:
                                        (SEQ ID NO: 19)
5'CTTTACACCAACCTCATAACCTTATC 3'

ZF_RASSF1 BT forward primer:
                                        (SEQ ID NO: 7)
5'TGCGTATGGTGGGCGAG3'

ZF_RASSF1 BT reverse primer:
                                        (SEQ ID NO: 8)
5'CCTAATTTACACGTCAACCAATCGAA3'

ZF_RASSF1 BT probe (Arm 5):
                                        (SEQ ID NO: 10)
5'CCACGGACGGCGCGTGCGTTT/3C6/

β-actin BT probe (Arm 3):
                                        (SEQ ID NO: 20)
5' GACGCGGAGATAGTGTTGTGG/3C6/3'

Arm3 QUASAR670:
                                        (SEQ ID NO: 21)
5'Q670/TCT/BHQ_2/AGCCGGTTTTCCGGCTGAGACTCCGCGTC/3C6

Arm5 FAM:
                                        (SEQ ID NO: 22)
5'd-FAM-TCT-BHQ-1-AGCCGGTTTTCCGGCTGAGACGTCCGTGG-C6
```

vi. Make a 20×Enzyme Mix containing the following:

200 mM MOPS, pH 7.5, 150 mM $MgCl_2$, 6.38 mM Tris-HCl, pH 8.0, 15.94 mM KCl, 2 μg/μl BSA, 0.16% Tween-20, 0.16% IGEPAL CA-630, 25% Glycerol, 146 ng/μl Cleavase 2.0, 1 unit/μL hotstart GoTaq polymerase.

vii. Set up QuARTS flap assay master mix, as follows (amount per reaction):

| Component | μL vol of stock to add per reaction |
|---|---|
| Water | 15.5 |
| 10X oligonucleotide/dNTP Mix | 3 |
| 20X Enzyme Mix | 1.5 |
| total volume master mix | 20 |

viii. For each reaction, combine 20 μl of QuARTS master mix with 10 μl of bisulfite-converted DNA.

ix. Seal plate with optical seal and put into LightCycler 480 and run profile das described in Example 2, detecting FAM signal for zebrafish DNA and QUASAR-670 signal for β-actin DNA:

x. Analyze the data using standard curves generated from dilution series of plasmids containing the sequences for bisulfite-converted β-actin and zebrafish DNA.

The results of the QuARTS assays performed pre- and post-bisulfite conversion are summarized below (each assay performed in duplicate):

Flap Assay Results for Untreated β-Actin DNA+/−Zebrafish DNA

| Sample ID | Zebrafish DNA | Ave ZF strands | STDEV | % CV | Ave β-actin Strands | STDEV | % CV |
|---|---|---|---|---|---|---|---|
| 4518 | − | 0 | 0 | | 86 | 2 | 3% |
| 4518 | + | 286 | 51 | 18% | 96 | 6 | 7% |
| 6133 | − | 0 | 0 | | 506 | 51 | 10% |
| 6133 | + | 264 | 31 | 12% | 293 | 21 | 7% |

Flap Assays for Bisulfite-Converted β-Actin DNA+/−Converted Zebrafish DNA

| Sample ID | Zebrafish Control | Ave ZF BT strands | STDEV | cv | Ave BT β-actin Strands | STDEV | % CV |
|---|---|---|---|---|---|---|---|
| 4518 | − | 0 | 0 | | 17210 | 207 | 1% |
| 4518 | + | 65306 | 4488 | 7% | 23217 | 355 | 2% |
| 6133 | − | 0 | 0 | | 384869 | 16254 | 4% |
| 6133 | + | 63170 | 3615 | 6% | 279081 | 25775 | 9% |

The signals obtained using the β-actin assays for untreated and bisulfite-converted DNA show that human DNA is present in the samples. The signals obtained using the zebrafish DNA assays for untreated and bisulfite-converted DNA show that the zebrafish assay reagents do not cross-react with either untreated or bisulfite-converted human DNA present in these samples.

Example 5

Comparison of Zebrafish DNA and β-Actin in DNA Extracted from Plasma

Assays were run to determine whether the presence of added zebrafish DNA altered the amount of extracted DNA detectable using the β-actin control.

Two plasma sample (Sample IDs 4517 and 4520) extractions were carried out with and without 12,000 copies of zebrafish DNA added prior to DNA extraction as described in Example 1. After extraction of the DNA, 10 μL of eluted DNA was assayed using a mixture of primers and probes directed to untreated (UT) β-actin and to zebrafish DNA, using a protocol as described in part B of Example 2. Two replicates were performed for each condition and the averaged measured strand counts for each type of DNA are shown in the table below (deviations are shows as next to the average strand value):

| Assay DNAs | | Assay Results | | | |
|---|---|---|---|---|---|
| | | Average | | Zebrafish | |
| Sample ID | Zebrafish DNA | β-actin Strands | Std Deviation | DNA Strands | Std Deviations |
| 4517 | – | 575 | 64 | 0 | 0 |
| 4517 | + | 435 | 53 | 567 | 11 |
| 4520 | – | 604 | 43 | 0 | 0 |
| 4520 | + | 440 | 114 | 627 | 100 |

The presence or absence of synthetic zebrafish DNA appears to have little or no effect on the average detected amounts of β-actin DNA, indicating that the zebrafish DNA does not interfere with recovery or detection of other DNA. Further, when zebrafish DNA is not added, no signal is generated for it, confirming that there is no cross-reactivity between zebrafish assay oligonucleotides for untreated DNA and the extracted human DNA.

Although the disclosure herein refers to certain illustrated embodiments, it is to be understood that these embodiments are presented by way of example and not by way of limitation. All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in molecular biology, biology, chemistry, biochemistry, medical sciences, or related fields are intended to be within the scope of the following claims.

We claim:

1. A composition comprising a mixture of DNA treated with a methylation-specific reagent system to form a treated DNA mixture, wherein the treated DNA mixture comprises:

a) isolated methylated zebrafish DNA or synthetic methylated DNA comprising a zebrafish DNA nucleotide sequence, and b) one or more of:

i) methylated DNA from a biological sample from a human, and ii) DNA from a eukaryotic cell from a human;

wherein the methylation-specific reagent system modifies nucleotides in DNA based on their methylation state to produce different nucleotides.

2. The composition of claim 1, wherein the methylation-specific reagent system modifies unmethylated cytosine nucleotides to produce different nucleotides.

3. The composition of claim 1, wherein the methylation-specific reagent system deaminates unmethylated cytosine nucleotides to produce deoxy uracil nucleotides.

4. The composition of claim 3, wherein the methylation-specific reagent system comprises a bisulfite reagent.

5. The composition of claim 1, wherein the methylation-specific reagent system modifies methylated cytosine nucleotides to produce different nucleotides.

6. The composition of claim 1, further comprising:

c) an oligonucleotide comprising a region complementary to treated methylated zebrafish DNA or treated synthetic methylated DNA comprising a zebrafish DNA nucleotide sequence; and d) an oligonucleotide comprising a region complementary to treated methylated DNA from a human.

7. The composition of claim 1, wherein the isolated methylated zebrafish DNA or the synthetic methylated DNA comprising a zebrafish DNA nucleotide sequence comprises at least a portion of zebrafish rassf1 gene DNA.

8. The composition of claim 1, wherein the treated DNA mixture further comprises at least one component from the group consisting of:

i) a bacterial, phage, viral, archaeal, or non-fish eukaryotic nucleic acid polymerase; and ii) a bacterial, phage, archaeal, or non-fish eukaryotic DNA modifying enzyme.

9. The composition of claim 8, wherein the nucleic acid polymerase is a thermostable DNA polymerase.

10. The composition of claim 8, wherein said DNA modifying enzyme comprises a ligase, an exonuclease, an endonuclease, and a FEN-1 flap endonuclease.

11. The composition of claim 1, wherein said biological sample from a human comprises one or more of blood, serum, plasma, tissue, stool, and sputum.

12. A method of treating methylated DNA from a human subject, comprising:

a) combining isolated methylated zebrafish DNA or synthetic methylated DNA comprising a zebrafish DNA nucleotide sequence with a sample comprising methylated DNA from a human in a mixture; and b) treating the mixture with a methylation-specific reagent system to form a treated DNA mixture, wherein the methylation-specific reagent system modifies nucleotides in DNA based on their methylation state to produce different nucleotides.

13. The method of claim 12, wherein the methylation-specific reagent system modifies unmethylated cytosine nucleotides to produce different nucleotides.

14. The method of claim 12, wherein the methylation-specific reagent system deaminates unmethylated cytosine nucleotides to produce deoxy uracil nucleotides.

15. The method of claim 12, wherein the methylation-specific reagent system comprises a bisulfite reagent.

16. The method of claim 12, wherein the sample comprising methylated DNA from a human comprises a biological sample containing methylated DNA from a human subject, and wherein prior to step b), the method comprises:

i) combining isolated methylated zebrafish DNA or synthetic methylated DNA comprising a zebrafish DNA nucleotide sequence with the biological sample in a combined sample; and ii) treating said combined sample to purify a DNA from the combined sample to provide the mixture of step a).

17. The method of claim 12, wherein the sample comprising methylated DNA from a human comprises one or more of:

i) DNA purified from a biological sample from a human; and ii) DNA purified from a eukaryotic cell from a human.

18. The method of claim 12, wherein the isolated methylated zebrafish DNA or the synthetic methylated DNA comprising a zebrafish DNA nucleotide sequence comprises at least a portion of zebrafish rassf1 gene DNA.

19. The method of claim 12, further comprising:

c) detecting treated isolated methylated zebrafish DNA or synthetic methylated DNA comprising a zebrafish DNA nucleotide sequence and treated methylated DNA from a human in the treated DNA mixture.

* * * * *

SEQUENCE LISTING

```
Sequence total quantity: 24
SEQ ID NO: 1           moltype = DNA  length = 2241
FEATURE                Location/Qualifiers
source                 1..2241
                       mol_type = other DNA
                       organism = Danio rerio
SEQUENCE: 1
tcagcaaatg aagtctgctc tccgttcgct cctcaaagta ggacagatcg cgccggatta  60
agcgttaatc tgagtcttct gcgcatgcgc atgaacgcgc gctacaagcg gacaaggtgc  120
gcgttcgaag aagaaacgaa ccgagccggt ttcgagcagc gacaacgcga atgaagccca  180
cggagtaccg aaaccttgag gaattcatct ttctgccagc ggaggactgt tttcagttta  240
gttttgagcg taatggaaga tgtttgggca cttttgcgca atccctcatg ttatcgcctc  300
acagacacgc gtcgcgcgcg cagattacgc ttaatttgag cggatttgag gaaacagacg  360
cgtttactgt cagtcgaggc tctactgaag actgaaagtg gcttgtttgg gtttaagatt  420
gacccagatg ctactgaaaa ctgtcaatca agaaggaaac tcttgaagca ataaaaacat  480
catctctgtt atatgaagac tgtcagatcc acacagtgat ccatgtttgt ggatatgcaa  540
acacatcaga acgagacgct aaatttatca gcttgctttg gagtaaacag cgttgcttta  600
aaacactcca cagtcataaa tcatctccag ccctaaccat ggtccactga gccatgccgt  660
tcatcctccc acgatcccaa aatggcaaaa tgtgagctca tcgagttgca ggacttgact  720
ccgaatgacc gtattgagct ggcacccccct agtgtccctc cacccaccgt ggtgcccact  780
ctggacaggt ggagcagagg gaaggtggtg cgcatggtgg gcgagcgcgt gcgcctggag  840
gaccccgatt ggctgacgtg taaaccagga cgaggacatg actttcagcc ctgcagccag  900
acacagctga gctggtgtga cctgtgtgga gagttcatct ggggcctgta cagacagagc  960
ctccgctgca cacactgtaa ctacacttgt cactaccgct gtcaaccctt cattcagctg  1020
gactgcagct ccaacaccga cactatctgc gaacaatcaa actacagcga ggacaccatc  1080
gagacagaca ccaatgtgga tgagcagtct gaagtggact ggaggaaaca ggatctgtct  1140
gtcactgaaa tacagcagaa agtgaaggaa tacaatgctc aggtcaacag taacctcttc  1200
atggttctga atcgtgacgg ctcatacact ggcttcatca aggtccagtt taagctggcg  1260
cgacccgtgt ctcttcctcc tccccgcagc gtctcctcct cctccatctc ctcctcttgt  1320
ttaggatggg atggcggctg tcaggagcga acttccttct acctgcccag agacacagtc  1380
aagcacctgc acatcagctc cagcacccgt gccagagagg tcatccaggc cctgctcaac  1440
aagttcactg tggtggacaa tccggctaaa tattccctgt atgagcgcag ccagcgggac  1500
```

```
aatcaagtgt acttaaggaa gttagctgat gatgaatgtc cacttttcct gcgtctgtgt  1560
gctggaccca atgagaaagt cctgagttta gtgcttaaag agaatgaaac cggggaagtg  1620
aattgggatg cgttcagttt tcctgaactc cagaacttcc tgcggattct ccagcgggag  1680
gaagaagatc acgtccggca aatcatacgc cgatacactc tggctcgtga taagatgaaa  1740
gaggctatga agaacttcag caagcctggc tgaatgaatc tgtgtttata cctcacaaac  1800
aagagagatc gaggaggaaa caaggcttat tactgtctga gtccaaagag tgtgtgaaag  1860
agcccttcgt cctactgtgg acataatgag ggttgaaagt gaaatgcagt gagcgagaga  1920
agagatgcgt gtgtttgaag catgactgtt gagtgtgact tcacactgga ggaaatgctg  1980
cgctcgtagc cgtagatcca gtggagagat gtcttcctgt ggagaatcta tatatcagtg  2040
cagattacag agtattttca gcaccattta aacttgtcat aggaaattaa acgaggatta  2100
ttttaatatc tgtatcaaaa tgccacctgt tagtgacaca gtaacttgtc atattttgaa  2160
gctcccatgt atatatttgg atgtttgttg tcaattattc tgaaaataga tacaaataaa  2220
ctatttttcc ctttaaaatg a                                            2241

SEQ ID NO: 2           moltype = DNA  length = 420
FEATURE                Location/Qualifiers
source                 1..420
                       mol_type = other DNA
                       organism = Danio rerio
SEQUENCE: 2
atcagaacga gacgctaaat ttatcagctt gctttggagt aaacagcgtt gctttaaaac  60
actcccacagt cataaatcat ctccagccct aaccatggtc cactgagcca tgccgttcat  120
cctcccacga tcccaaaatg gcaaaatgtg agctcatcga gttgcaggac ttgactccga  180
atgaccgtat tgagctggca ccccctagtg tccctccacc caccgtggtg cccactctgg  240
acaggtggag cagagggaag gtggtgcgca tggtgggcga gcgcgtgcgc ctggaggacc  300
ccgattggct gacgtgtaaa ccaggacgag gacatgactt tcagccctgc agccagacac  360
agctgagctg gtgtgacctg tgtggagagt tcatctgggg cctgtacaga cagagcctcc  420

SEQ ID NO: 3           moltype = DNA  length = 420
FEATURE                Location/Qualifiers
source                 1..420
                       mol_type = other DNA
                       organism = Danio rerio
SEQUENCE: 3
attagaacga gacgttaaat ttattagttt gttttggagt aaatagcgtt gttttaaaat  60
attttatagt tataaattat ttttagtttt aattatggtt tattgagtta tgtcgtttat  120
ttttttacga ttttaaaatg gtaaaatgtg agtttatcga gttgtaggat ttgatttcga  180
atgatcgtat tgagttggta ttttttagtg tttttttatt tatcgtggtg tttattttgg  240
ataggtggag tagagggaag gtggtgcgta tggtgggcga gcgcgtgcgt ttggaggatt  300
tcgattggtt gacgtgtaaa ttaggacgag gatatgattt ttagttttgt agttagatat  360
agttgagttg gtgtgatttg tgtggagagt ttatttgggg tttgtataga tagagttttc  420

SEQ ID NO: 4           moltype = DNA  length = 15
FEATURE                Location/Qualifiers
source                 1..15
                       mol_type = other DNA
                       organism = synthetic construct
SEQUENCE: 4
cgcatggtgg gcgag                                                   15

SEQ ID NO: 5           moltype = DNA  length = 18
FEATURE                Location/Qualifiers
source                 1..18
                       mol_type = other DNA
                       organism = synthetic construct
SEQUENCE: 5
acacgtcagc caatcggg                                                18

SEQ ID NO: 6           moltype = DNA  length = 20
FEATURE                Location/Qualifiers
source                 1..20
                       mol_type = other DNA
                       organism = synthetic construct
SEQUENCE: 6
gacgcggagg cgcgtgcgcc                                              20

SEQ ID NO: 7           moltype = DNA  length = 17
FEATURE                Location/Qualifiers
source                 1..17
                       mol_type = other DNA
                       organism = synthetic construct
SEQUENCE: 7
tgcgtatggt gggcgag                                                 17

SEQ ID NO: 8           moltype = DNA  length = 26
FEATURE                Location/Qualifiers
source                 1..26
                       mol_type = other DNA
                       organism = synthetic construct
```

```
SEQUENCE: 8
cctaatttac acgtcaacca atcgaa                                    26

SEQ ID NO: 9            moltype = DNA  length = 21
FEATURE                 Location/Qualifiers
source                  1..21
                        mol_type = other DNA
                        organism = synthetic construct
SEQUENCE: 9
gacgcggagg cgcgtgcgtt t                                         21

SEQ ID NO: 10           moltype = DNA  length = 21
FEATURE                 Location/Qualifiers
source                  1..21
                        mol_type = other DNA
                        organism = synthetic construct
SEQUENCE: 10
ccacggacgg cgcgtgcgtt t                                         21

SEQ ID NO: 11           moltype = DNA  length = 171
FEATURE                 Location/Qualifiers
source                  1..171
                        mol_type = other DNA
                        organism = synthetic construct
SEQUENCE: 11
tccacgtggt gcccactctg gacaggtgga gcagagggaa ggtggtggca tggtggggag  60
ggtggcctgg aggacccgat tggctgagtg taaaccagga gaggacatga ctttcagccc  120
tgcagccaga cacagctgag ctggtgtgac ctgtgtggag agttcatctg g           171

SEQ ID NO: 12           moltype = DNA  length = 171
FEATURE                 Location/Qualifiers
source                  1..171
                        mol_type = other DNA
                        organism = synthetic construct
SEQUENCE: 12
ccagatgaac tctccacaca ggtcacacca gctcagctgt gtctggctgc agggctgaaa  60
gtcatgtcct gtcctggttt acagtcagcc aatggggtcc tccagggcag gctgcccacc  120
atggcaccac cttccctctg ctccacctgt ccagagtggg caccaggtgg a           171

SEQ ID NO: 13           moltype = DNA  length = 224
FEATURE                 Location/Qualifiers
source                  1..224
                        mol_type = other DNA
                        organism = synthetic construct
SEQUENCE: 13
ctctgacctg agtctccttt ggaactctgc aggttctatt tgctttttcc cagatgagct  60
ctttttctgg tgtttgtctc tctgactagg tgtctaagac agtgttgtgg gtgtaggtac  120
taacactggc tcgtgtgaca aggccatgag gctggtgtaa agcggccttg gagtgtgtat  180
taagtaggtg cacagtaggt ctgaacagac tccccatccc aaga                   224

SEQ ID NO: 14           moltype = DNA  length = 224
FEATURE                 Location/Qualifiers
source                  1..224
                        mol_type = other DNA
                        organism = synthetic construct
SEQUENCE: 14
ttttgatttg agttttttt ggaattttgt aggttttatt tgtttttttt tagatgagtt  60
tttttttgg tgtttgtttt tttgattagg tgtttaagat agtgttgtgg gtgtaggtat  120
taatattggt ttgtgtgata aggttatgag gttggtgtaa agtggttttg gagtgtgtat  180
taagtaggtg tatagtaggt ttgaatagat tttttatttt aaga                   224

SEQ ID NO: 15           moltype = DNA  length = 19
FEATURE                 Location/Qualifiers
source                  1..19
                        mol_type = other DNA
                        organism = synthetic construct
SEQUENCE: 15
ccatgaggct ggtgtaaag                                            19

SEQ ID NO: 16           moltype = DNA  length = 24
FEATURE                 Location/Qualifiers
source                  1..24
                        mol_type = other DNA
                        organism = synthetic construct
```

```
SEQUENCE: 16
ctactgtgca cctacttaat acac                                        24

SEQ ID NO: 17          moltype = DNA  length = 20
FEATURE                Location/Qualifiers
source                 1..20
                       mol_type = other DNA
                       organism = synthetic construct
SEQUENCE: 17
cgccgagggc ggccttggag                                             20

SEQ ID NO: 18          moltype = DNA  length = 30
FEATURE                Location/Qualifiers
source                 1..30
                       mol_type = other DNA
                       organism = synthetic construct
SEQUENCE: 18
gtgtttgttt ttttgattag gtgtttaaga                                  30

SEQ ID NO: 19          moltype = DNA  length = 26
FEATURE                Location/Qualifiers
source                 1..26
                       mol_type = other DNA
                       organism = synthetic construct
SEQUENCE: 19
ctttacacca acctcataac cttatc                                      26

SEQ ID NO: 20          moltype = DNA  length = 21
FEATURE                Location/Qualifiers
source                 1..21
                       mol_type = other DNA
                       organism = synthetic construct
SEQUENCE: 20
gacgcggaga tagtgttgtg g                                           21

SEQ ID NO: 21          moltype = DNA  length = 29
FEATURE                Location/Qualifiers
source                 1..29
                       mol_type = other DNA
                       organism = synthetic construct
SEQUENCE: 21
agccggtttt ccggctgaga ctccgcgtc                                   29

SEQ ID NO: 22          moltype = DNA  length = 29
FEATURE                Location/Qualifiers
source                 1..29
                       mol_type = other DNA
                       organism = synthetic construct
SEQUENCE: 22
agccggtttt ccggctgaga cgtccgtgg                                   29

SEQ ID NO: 23          moltype = DNA  length = 19
FEATURE                Location/Qualifiers
source                 1..19
                       mol_type = other DNA
                       organism = synthetic construct
SEQUENCE: 23
gcgcgtccgc gcgtgcgcc                                              19

SEQ ID NO: 24          moltype = DNA  length = 28
FEATURE                Location/Qualifiers
source                 1..28
                       mol_type = other DNA
                       organism = synthetic construct
SEQUENCE: 24
agccggtttt ccggctgaga ggacgcgc                                    28
```